United States Patent [19]

Hutchison et al.

[11] Patent Number: 5,034,381
[45] Date of Patent: Jul. 23, 1991

[54] 2-(SUBSTITUTED AMINO) ADENOSINES AS ANTIHYPERTENSIVES

[75] Inventors: Alan J. Hutchison, Verona; John E. Francis, Basking Ridge, both of N.J.

[73] Assignee: Ciba-Geigy Corporation, Ardsley, N.Y.

[21] Appl. No.: 193,968

[22] Filed: May 13, 1988

Related U.S. Application Data

[63] Continuation-in-part of Ser. No. 142,055, Jan. 7, 1988, abandoned.

[51] Int. Cl.$^5$ .................... A61K 31/70; C07H 19/167
[52] U.S. Cl. ...................................... 514/26; 514/45; 536/26; 536/24
[58] Field of Search .................... 536/24, 26; 514/45, 514/46

[56] References Cited

U.S. PATENT DOCUMENTS

| | | | |
|---|---|---|---|
| 3,590,029 | 6/1971 | Koch et al. | 260/211.5 |
| 3,838,147 | 9/1974 | Pohlko et al. | 260/211.5 R |
| 3,917,583 | 11/1975 | Meyer et al. | 536/22 |
| 4,258,033 | 3/1981 | Marumoto et al. | 424/180 |
| 4,341,769 | 7/1982 | Marumoto et al. | 424/180 |
| 4,501,735 | 2/1985 | Triveda et al. | 514/46 |
| 4,593,019 | 6/1986 | Bristol et al. | 514/46 |
| 4,594,350 | 6/1986 | Vince | 514/261 |
| 4,600,707 | 7/1986 | Patt | 514/46 |
| 4,683,223 | 7/1987 | Trivedi | 514/46 |
| 4,791,103 | 12/1988 | Trivedi et al. | 514/46 |
| 4,843,066 | 6/1989 | Yamada et al. | 514/45 |

FOREIGN PATENT DOCUMENTS

| | | |
|---|---|---|
| 152944 | of 1985 | European Pat. Off. |
| 232813 | of 1987 | European Pat. Off. |
| 0269574 | 6/1988 | European Pat. Off. |
| 50-101383 | of 1975 | Japan |
| 8504882 | of 1985 | World Int. Prop. O. |

OTHER PUBLICATIONS

Chem. & Pharma. Bulletin 27, 990–1003 (1979).
Daly et al., Biochemical Pharmacology, vol. 35, No. 15, pp. 2467–2481 (1986).
Journal of Medicinal Chemistry, vol. 28, No. 10, pp. 1383–1384 (1985).
Omura et al., Chem. Pharm. Bull., vol. 29, No. 7, pp. 1870–1875 (1981).
Hamilton et al., Life Sciences, vol. 41, pp. 2295–2302 (1987).
Marumoto et al., J. Takeda Res. Labs., vol. 44, pp. 220–230 (1985).
Chem. Abstr. 94: 140119m (1981).
Chem. Abstr. 84: 74578a (1976).
Ryuji Marumoto et al., Chem. Pharm. Bull. 23 (4) 759–774 (1975).
Annual Reports in Medicinal Chemistry, vol. 23, 1988, pp. 39–48, Alexander J. Bridges et al.

Primary Examiner—Johnnie R. Brown
Assistant Examiner—L. Eric Crane
Attorney, Agent, or Firm—Norbert Gruenfeld

[57] ABSTRACT

Disclosed are 2-substituted adenosine derivatives of the formula

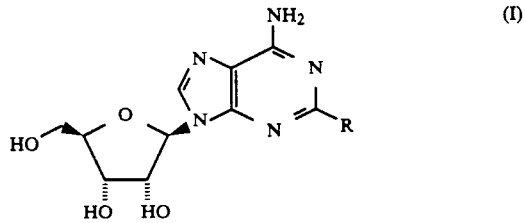

(I)

in which R represents a substituted amino grouping of the formula

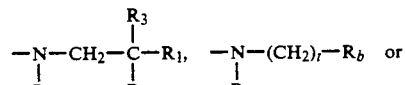

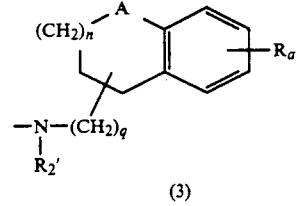

(3)

as defined herein; pharmaceutically acceptable ester derivatives thereof in which free hydroxy groups are esterified in the form of a pharmaceutically acceptable prodrug ester; and pharmaceutically acceptable salts thereof; pharmaceutical compositions comprising said compounds; methods for their preparation; and their use in mammals as therapeutically effective adenosine-2 (A-2) agonists.

22 Claims, No Drawings

2-(SUBSTITUTED AMINO) ADENOSINES AS ANTIHYPERTENSIVES

CROSS-REFERENCE TO RELATED APPLICATIONS

This is a continuation-in-part of application Ser. No. 142,055 filed Jan. 7, 1988, now abandoned.

SUMMARY OF THE INVENTION

The instant invention is directed to certain 2-substituted adenosine derivatives as adenosine receptor ligands, to pharmaceutical compositions thereof, to methods for their preparation, and to their use in mammals as therapeutically effective adenosine-2 (A-2) agonists.

The compounds of the invention are effective adenosine-2 (A-2) receptor ligands which are useful in mammals as adenosine-2 (A-2) agonists.

Said advantageous properties render the compounds of the invention useful for the treatment of conditions in mammals responsive to selective adenosine-2 agonist activity e.g. cardiovascular conditions such as hypertension, thrombosis and atherosclerosis.

DETAILED DESCRIPTION OF THE INVENTION

The instant invention is directed to the 2-substituted adenosine derivatives of the formula I

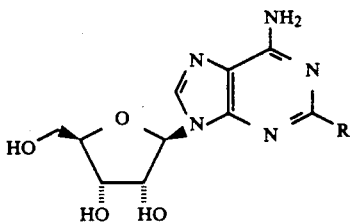

wherein the substituent R represents

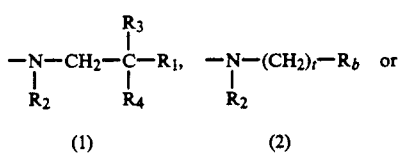

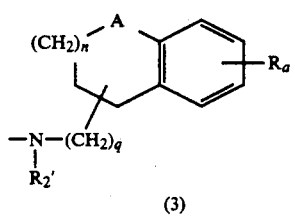

as defined herein; pharmaceutically acceptable ester derivatives thereof in which free hydroxy groups are esterified in the form of a pharmaceutically acceptable prodrug ester; and pharmaceutically acceptable salts thereof.

More specifically, the instant invention is directed to the compounds of the formula II

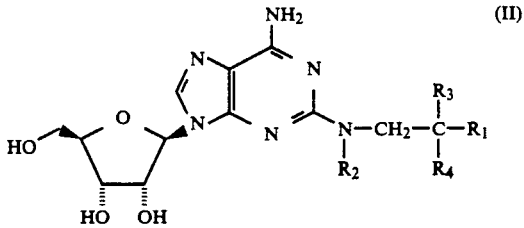

(a) wherein $R_1$ represents phenyl substituted by a substituent -W-Z in which W represents a direct bond, lower alkenylene, lower alkylene, thio-lower alkylene or oxy-lower alkylene and Z represents cyano, carboxy or carboxy derivatized in the form of a pharmaceutically acceptable ester or amide; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (b) wherein $R_1$ represents phenyl or phenyl substituted by one to three of lower alkyl, lower alkoxy, hydroxy, lower alkanoyloxy, halogen, benzyloxy or trifluoromethyl; $R_2$ represents hydrogen or lower alkyl; $R_3$ represent hydrogen, lower alkyl or hydroxy, and $R_4$ represents hydrogen or lower alkyl, with the proviso that $R_2$ does not represent hydrogen if both $R_3$ and $R_4$ represent hydrogen; pharmaceutically acceptable prodrug ester derivatives thereof in which one or more free hydroxy groups are esterified in form of a pharmaceutically acceptable ester; and pharmaceutically acceptable salts thereof; or (c) wherein $R_1$ represents a heterocyclic aromatic radical, particularly pyridyl, thienyl, pyrrolyl or indolyl, each optionally substituted by halogen, lower alkyl or -W-Z as defined under (a); $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (d) wherein $R_1$ represents $C_3$-$C_7$-cycloalkyl; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (e) wherein the —$CR_1R_3R_4$ moiety as a single group represents 9-fluorenyl; $R_2$ represents hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (f) wherein $R_1$ represents either phenyl or $C_5$-$C_7$-cycloalkyl alkyl substituted by a substituent -W-Z in which W represents lower alkylene and Z represents hydroxy; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (g) wherein $R_1$ represents phenyl substituted by -W-Z, in which W represents lower alkylene or lower alkenylene and Z represents phenyl or $C_5$-$C_7$ cycloalkyl; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (h) wherein $R_1$ represents $C_5$-$C_7$-cycloalkyl substituted by a substituent-W-Z in which W represents a direct bond or lower alkylene and Z represents carboxy or carboxy derivatized in the form of a pharmaceutically acceptable ester or amide, or substituted by one or two of lower alkyl, hydroxy, lower alkanoyloxy or lower alkoxy, or substituted by lower alkylenedioxy in which the two oxygen atoms are attached to the same carbon atom or on adjacent carbon atoms; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (i) wherein $R_1$ represents bicycloheptyl optionally substituted by lower alkyl, bicycloheptenyl optionally substituted by lower alkyl, or adamantyl; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof; or (j) wherein $R_1$ represents cyclohexenyl or cyclohexenyl substituted by lower alkyl; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof.

(k) wherein $R_1$ represents tetrahydropyranyl or tetrahydrothiopyranyl; $R_2$ represents hydrogen or lower alkyl; $R_3$ and $R_4$ independently represent hydrogen or lower alkyl; pharmaceutically acceptable prodrug ester derivatives thereof in which one or more free hydroxy groups are esterified in form of a pharmaceutically acceptable ester; and pharmaceutically acceptable salts thereof.

The instant invention is further directed to the compounds of formula IIa

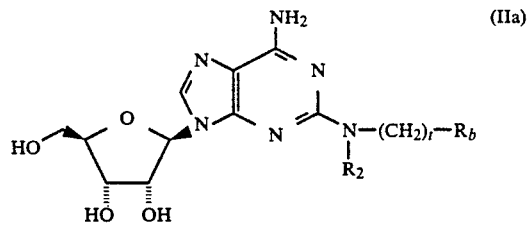

wherein $R_2$ represents hydrogen or lower alkyl; t represents the integer 3, 4, 5 or 6; and $R_b$ represents (a) $C_3$-$C_7$-cycloalkyl optionally substituted by lower alkyl;

(b) cyclohexenyl optionally substituted by lower alkyl;

(c) bicycloheptyl optionally substituted by lower alkyl;

(d) bicycloheptenyl optionally substituted by lower alkyl;

(e) a heterocyclic aromatic radical, particularly pyridyl, thienyl, pyrrolyl or indolyl, each optionally substituted by lower alkyl or halogen; or (f) phenyl or phenyl substituted by halogen, lower alkyl, lower alkoxy, trifluoromethyl, cyano, carboxy, lower alkoxycarbonyl, carbamoyl, N-mono- or N,N-di-lower alkylcarbamoyl; pharmaceutically acceptable prodrug ester derivatives thereof in which one or more free hydroxy groups are esterified in form of a pharmaceutically acceptable ester; and pharmaceutically acceptable salts thereof.

The instant invention is also directed to the compounds of the formula III

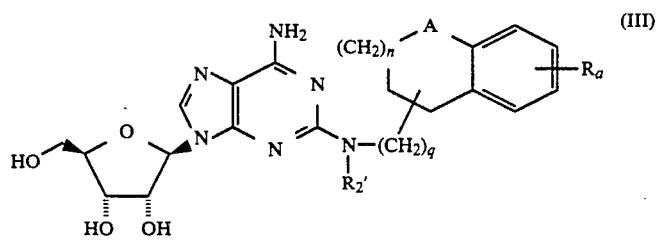

in which A represents methylene, oxy or thio, n represents zero or one, q represents zero, one or two, and $R_a$ represents hydrogen, lower alkyl, lower alkoxy, halogen or -W-Z in which W represents a direct bond, lower alkenylene, lower alkylene, thio-lower alkylene or oxy-lower alkylene, and Z represents cyano, carboxy, carboxy derivatized in the form of a pharmaceutically acceptable ester or carboxy derivatized in the form of a pharmaceutically acceptable amide; and $R_2'$ represents hydrogen or lower alkyl; pharmaceutically acceptable prodrug ester derivatives thereof in which one or more free hydroxy groups are esterified in the form of a pharmaceutically acceptable ester; and pharmaceutically acceptable salts thereof.

As to the compounds represented by formula II, preferred embodiments relate to the compounds of formula II wherein $R_2$ and $R_4$ represent hydrogen; $R_3$ represents hydrogen or lower alkyl; and $R_1$ represents:

phenyl substituted by a substituent -W-Z in which W represents a direct bond, lower alkenylene, lower alkylene, thio-lower alkylene or oxy-lower alkylene and Z represents cyano, carboxy or carboxy derivatized in the form of a pharmaceutically acceptable ester or amide, $C_5$–$C_7$-cycloalkyl, $C_5$–$C_7$-cycloalkyl substituted by a substituent -W-Z in which W represents a direct bond or lower alkylene and Z represents carboxy or carboxy derivatized in the form of a pharmaceutically acceptable ester or amide, or $C_5$–$C_7$-cycloalkyl substituted by one or two of lower alkyl, hydroxy, lower alkanoyloxy or lower alkoxy, or substituted by lower alkylenedioxy in which the two oxygen atoms are attached to the same carbon atom or on adjacent carbon atoms, bicycloheptyl optionally substituted by lower alkyl, bicycloheptenyl optionally substituted by lower alkyl, adamantyl, cyclohexenyl optionally substituted by lower alkyl, tetrahydropyranyl or tetrahydrothiopyranyl;

pharmaceutically acceptable prodrug ester derivatives thereof in which one or more free hydroxy groups are esterified in form of a pharmaceutically acceptable ester; and pharmaceutically acceptable salts thereof.

A preferred embodiment of the invention relating to the compounds of formula II cited under (a) involves the compounds of the formula II wherein $R_1$ represents phenyl monosubstituted by a substituent -W-Z in which W represents a direct bond, straight chain or branched $C_1$–$C_4$-alkylene, thio-$C_1$–$C_3$-alkylene or oxy-$C_1$–$C_3$-alkylene, and Z represents cyano, carboxy, lower alkoxycarbonyl, carbamoyl, N-mono- or N,N-di-lower alkylcarbamoyl; $R_2$ and $R_3$ independently represent hydrogen or $C_1$–$C_4$-alkyl; $R_4$ represents hydrogen; pharmaceutically acceptable prodrug ester derivatives thereof in which one or more free hydroxy groups are esterified in form of a pharmaceutically acceptable prodrug ester; and pharmaceutically acceptable salts thereof.

Further preferred are said compounds of the formula II wherein W represents straight chain or branched $C_2$–$C_4$-alkylene or oxy-straight chain or branched $C_1$–$C_3$-alkylene in each of which the phenyl ring and Z are separated by a chain of two or three atoms; pharmaceutically acceptable prodrug esters as cited above; and pharmaceutically acceptable salts.

Particularly preferred are said compounds of formula II wherein W represents ethylene, propylene, oxymethylene or oxyethylene; pharmaceutically acceptable prodrug esters as cited above; and pharmaceutically acceptable salts.

Particularly preferred are the compounds of the formula IV

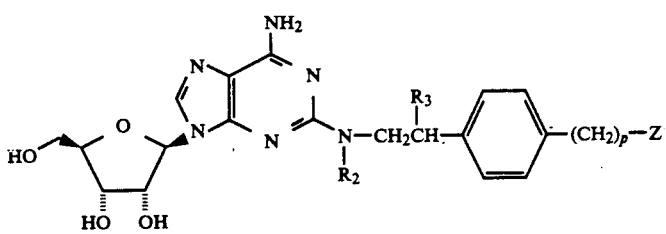

(IV)

wherein $R_2$ and $R_3$ independently represent hydrogen or $C_1$–$C_4$-alkyl; p represents the integer 1 or 2; Z represents phenyl, carboxy, lower alkoxycarbonyl, carbamoyl, N-mono- or N,N-di-lower alkylcarbamoyl; pharmaceutically acceptable prodrug ester derivatives thereof in which one or more free hydroxy groups are esterified in form of a pharmaceutically acceptable prodrug ester thereof; and pharmaceutically acceptable salts thereof.

Further preferred are said compounds of formula IV wherein $R_2$ and $R_3$ independently represent hydrogen, methyl or ethyl; p represents the integer 2, and Z represents carboxy or lower alkoxycarbonyl; pharmaceutically acceptable prodrug esters as cited above; and pharmaceutically acceptable salts. Most preferred are the said compounds wherein $R_2$ and $R_3$ represent hydrogen and Z represents carboxy or lower alkoxycarbonyl.

A preferred embodiment relating to the compounds of formula II cited under (b) above involves the compounds of formula II wherein $R_1$ represents phenyl or phenyl monosubstituted by lower alkyl, lower alkoxy, benzyloxy or halogen; $R_2$ and $R_4$ independently represent hydrogen or $C_1$–$C_4$-alkyl; and $R_3$ represents $C_1$–$C_4$-alkyl or hydroxy; pharmaceutically acceptable prodrug ester derivatives thereof in which one or more free hydroxy groups are esterified in form of a pharmaceutically acceptable ester; and pharmaceutically acceptable salts thereof. Preferred are said compounds wherein $R_2$ represents hydrogen or methyl; $R_3$ represents methyl or hydroxy; and $R_4$ represents hydrogen.

Another preferred embodiment relating to the compounds of formula II cited under (b) above involves the compounds of formula II wherein $R_1$ represents phenyl or phenyl monosubstituted by lower alkyl, lower alkoxy or halogen; $R_2$ represents methyl; $R_3$ and $R_4$ independently represent hydrogen or $C_1$–$C_4$-alkyl; pharmaceutically acceptable prodrug ester derivatives thereof in which one or more free hydroxy groups are esterified in form of a pharmaceutically acceptable ester; and pharmaceutically acceptable salts thereof. Preferred are said compounds wherein $R_2$ represents methyl; and $R_3$ and $R_4$ represent hydrogen.

A preferred embodiment relating to the compounds of formula II cited under (c) above involves the compounds of formula II wherein $R_1$ represents 2-pyridyl or 2-thienyl; $R_2$ represents hydrogen or lower alkyl; $R_3$ and $R_4$ represent hydrogen; pharmaceutically acceptable prodrug ester derivatives thereof in which one or more free hydroxy groups are esterified in form of a pharmaceutically acceptable ester; and pharmaceutically acceptable salts thereof.

A preferred embodiment relating to the compounds of formula II cited under (d) above involves the compounds of formula II wherein $R_1$ represents cyclohexyl or cyclopentyl; $R_2$ and $R_4$ represent hydrogen; $R_3$ represents hydrogen or $C_1$–$C_4$-alkyl; pharmaceutically acceptable prodrug ester derivatives thereof in which one or more free hydroxy groups are esterified in form of a pharmaceutically acceptable ester; and pharmaceutically acceptable salts thereof. Preferred are said compounds wherein $R_1$ represents cyclohexyl.

Preferred embodiments relating to the compounds of formula II cited under (a) and (c) through (k) involve compounds wherein $R_2$, $R_3$ and $R_4$ represent hydrogen.

Also preferred are the compounds of formula IIa wherein $R_2$ represents hydrogen, and the compounds of formula IV wherein $R_2$ and $R_3$ represent hydrogen.

A preferred embodiment of the compounds of formula III relate to the compounds of formula III wherein n represents the integer 1; q is zero; A represents a direct bond, methylene, oxy or thio; $R_a$ represents hydrogen, lower alkyl, lower alkoxy, hydroxy, halogen, or -W-Z in which W represents a direct bond, $C_1$-$C_4$-alkylene, thio-$C_1$-$C_3$-alkylene or oxy-$C_1$-$C_3$-alkylene, and Z represents cyano, carboxy, lower alkoxycarbonyl, carbamoyl, N-mono- or N,N-di-lower alkylcarbamoyl; $R_2'$ represents hydrogen; pharmaceutically acceptable prodrug ester derivatives thereof in which one or more free hydroxy groups are esterified in form of a pharmaceutically acceptable ester; and pharmaceutically acceptable salts thereof.

Preferred are said above compounds of formula III wherein $R_a$ and $R_2'$ represent hydrogen; n, q and A have meaning as defined above; pharmaceutically acceptable prodrug ester derivatives thereof in which one or more free hydroxy groups are esterified in form of a pharmaceutically acceptable ester; and pharmaceutically acceptable salts thereof.

In said compounds of formula III, the 2-substituent of partial structure (3) corresponding to R in formula I, preferably represents 1,2,3,4-tetrahydro-2-naphthylamino, 2-indanylamino, 3,4-dihydro-2H-[1]-3-benzopyranylamino or 3,4-dihydro-2H-[1]-3-benzothiopyranylamino, or any of said grouping substituted on the benzo portion by lower alkyl, lower alkoxy, halogen or W-Z as defined hereinabove.

The compounds of the invention, of formula I to IV and derivatives thereof, all contain the optically pure β-D-ribofuranosyl moiety and are thus optically active. In addition, compounds of the invention may contain one or more asymmetric carbon atoms within the 2-substituent (R in formula I).

Thus, the compounds of the invention can exist in the form of pure enantiomers or diastereoisomers, or mixtures thereof, all of which are within the scope of the invention.

The general definitions used herein have the following meaning within the scope of the present invention.

The term "lower" referred to above and hereinafter in connection with organic radicals or compounds respectively defines such with up to and including 7, preferably up to and including 4 and advantageously one or two carbon atoms.

A lower alkyl group is straight chain or branched and preferably contains 1 to 4 carbon atoms, and represents for example methyl, ethyl, propyl, butyl, advantageously methyl.

A lower alkoxy group is straight chain or branched and preferably contains 1 to 4 carbon atoms, and represents for example methoxy, ethoxy, propoxy.

Lower alkylene is straight chain or branched alkylene and preferably contains 1 to 4 carbon atoms, and represents for example methylene, ethylene.

lower alkenylene preferably contains 2 to 4 carbon atoms and represents for example ethenylene or propenylene.

$C_3$-$C_7$-cycloalkyl represents cyclopropyl, cyclobutyl, cyclopentyl, cyclohexyl or cycloheptyl, preferably cyclopentyl, cyclohexyl, or cyclopropyl.

$C_5$-$C_7$-cycloalkyl represents cyclopentyl, cyclohexyl or cycloheptyl, preferably cyclohexyl.

Halogen is preferably chloro, but may also be fluoro, bromo or iodo.

Cyclohexenyl represents preferably 1-cyclohexenyl.

Cycloalkenyl-lower alkyl represents preferably 1-cyclohexenyl-lower alkyl.

Bicycloheptyl optionally substituted by lower alkyl represents preferably unsubstituted or lower alkyl substituted bicyclo[2.2.1]heptyl, such as bornyl, neobornyl, isobornyl, norbornyl, e.g. 2-norbornyl, or unsubstituted or lower alkyl-substituted bicyclo[3.2.1]-heptyl, e.g. 6,6-dimethyl-bicyclo[3.1.1]hept-2-yl. The term bornyl is synonymous with bornanyl.

Bicycloheptenyl optionally substituted by lower alkyl represents preferably unsubstituted or lower alkyl-substituted bicyclo[2.2.1]heptenyl, such as norborn-5-en-2-yl, or bicyclo[3.1.1]heptenyl such as 6,6-dimethyl-bicyclo[3.1.1]hept-2-en-2-yl.

Adamantyl represents preferably 1-adamantyl.

A heterocyclic aromatic radical represents in particular pyridyl, thienyl, pyrrolyl or indolyl.

Pyridyl represents 2-, 3- or 4-pyridyl, advantageously 2- or 3-pyridyl.

Thienyl represents 2- or 3-thienyl, advantageously 2-thienyl.

Indolyl represents 2- or 3-indolyl, advantageously 3-indolyl.

Pyrrolyl represents 1,2 or 3-pyrrolyl advantageously 1-pyrrolyl.

Tetrahydropyranyl and tetrahydrothiopyranyl represents preferably 4-tetrahydropyranyl and 4-tetrahydrothiopyranyl, respectively.

A lower alkoxycarbonyl group preferably contains 1-4 carbon atoms in the alkoxy portion and represents for example: methoxycarbonyl, propoxycarbonyl, isopropoxycarbonyl or advantageously ethoxycarbonyl.

A lower alkanoic acid represents preferably a straight chain or branched $C_1$-$C_4$-alkanoic acid, e.g. acetic, isobutyric, pivaloi acid. Preferred lower alkanoyl groups are those derived therefrom.

A lower alkoxy-lower alkanoic acid represents preferably a lower alkoxy-$C_2$-$C_4$-alkanoic acid, e.g. methoxyacetic, 3-ethoxypropionic acid. Preferred lower alkoxy-lower alkanoyl groups are those derived therefrom.

An arylcarboxylic acid represents preferably benzoic acid, benzoic acid substituted by one to three of lower alkyl, lower alkoxy, halogen or trifluoromethyl; 2-, 3- or 4-pyridylcarboxylic acid, or 2- or 3-thienylcarboxylic acid. Preferred arylcarbonyl groups are those derived therefrom.

Mono- and di-lower alkylcarbamoyl represents for example N-methyl-, N-ethyl-, N,N-dimethyl- and N,N-diethylcarbamoyl.

Carboxy esterified in form of a pharmaceutically acceptable ester represents advantageously an ester that may be convertible by solvolysis or under physiological conditions to the free carboxylic acid, e.g. lower alkoxycarbonyl; (amino, mono- or di-lower alkylamino)-substituted lower alkoxycarbonyl; carboxy substituted lower alkoxycarbonyl, e.g. alpha-carboxy-substituted lower alkoxycarbonyl; lower alkoxycarbonyl-substituted lower alkoxycarbonyl, e.g. alpha-lower alkoxycarbonyl-substituted lower alkoxycarbonyl; aryl-substituted lower alkoxycarbonyl, e.g. optionally substituted benzyloxycarbonyl or pyridylmethoxycarbonyl; (hydroxy, lower alkanoyloxy or lower alkoxy)-substituted lower alkoxy carbonyl, e.g. pivaloyloxymethoxycarbonyl; (hydroxy, lower alkanoyloxy or lower alkoxy)-substituted lower alkoxymethoxycarbonyl; bicycloalkoxycarbonyl-substituted lower alkoxycarbonyl, e.g. bicyclo[2,2,1]-heptyloxycarbonyl-substituted lower alkoxycarbonyl, especially bicyclo[2,2,1]-heptyloxycarbonyl-substituted methoxycarbonyl such as bornyloxycarbonylmethoxycarbonyl; 3-phthalidoxycarbonyl; (lower alkyl, lower alkoxy, halo)-substituted 3-phthalidoxycarbonyl; lower alkoxycarbonyloxy-lower alkoxycarbonyl, e.g. 1-(methoxy- or ethoxycarbonyloxy)-ethoxycarbonyl; aryloxycarbonyl, e.g. phenoxycarbonyl or phenoxycarbonyl advantageously substituted at the ortho position by carboxy or lower alkoxycarbonyl.

Carboxy derivatized in form of a pharmaceutically acceptable amide represents preferably carbamoyl, mono-N-lower alkylcarbamoyl or N,N-di-lower alkylcarbamoyl.

The pharmaceutically acceptable prodrug ester derivatives in which one or more free hydroxy groups are esterified in the form of a pharmaceutically acceptable ester are particularly prodrug esters that may be convertible by solvolysis under physiological conditions to the compounds of formula I having free hydroxy groups. Preferred are the mono esters in which the 5-hydroxy group of the ribosyl grouping is esterified.

Preferred as said prodrug pharmaceutically acceptable esters are straight chain or branched lower alkanoic acid esters, e.g., the acetic, isobutyric, pivaloic acid esters; lower alkoxy-lower alkanoic acid esters, e.g., the methoxyacetic, 3-ethoxypropionic acid esters; arylcarboxylic acid esters, e.g., the benzoic, nicotinic acid esters; carbamic and mono or di-lower alkylcarbamic acid esters (carbamates), e.g. the mono- or di-ethylcarbamic or N-mono- or di-methylcarbamic acid esters. Most preferred are the lower alkanoic acid and lower alkoxyalkanoic acid esters.

Preferred are the said mono esters in which the 5-hydroxy group of the ribosyl grouping is esterified.

Pharmaceutically acceptable salts are generally acid addition salts, which are preferably such of therapeutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

Pharmaceutically acceptable salts of the compounds of the invention having a free carboxy group are formed with pharmaceutically acceptable bases, such as alkali metal, alkaline earth metal, copper or zinc hydroxides, ammonia, mono-, di- or tri-lower (alkyl or hydroxyalkyl)-amines, monocyclic amines or alkylene-diamines, and are e.g. the sodium, potassium, magnesium, calcium, ammonium, mono-, di- or tri-(methyl, ethyl or hydroxyethyl)-amine or tris-(hydroxymethyl)-methylamine salts.

The novel compounds of the invention are active in state of the art in vitro and in vivo test systems, indicative of selective adenosine agonist activity in mammals.

The compounds of the invention are useful as selective adenosine-2 agonists in mammals including man, particularly for the treatment of cardiovascular disorders, such as hypertension and thrombosis.

The above-cited properties are demonstrable in in vitro and in vivo tests, using advantageously mammals, e.g. rats, dogs, monkeys or isolated organs, tissues and preparations thereof. Said compounds can be applied in vitro in the form of solutions, e.g. preferably aqueous solutions, and in vivo either enterally or parenterally advantageously orally or intravenously, e.g. within gelatin capsules, as starch suspensions or in aqueous solutions. The dosage in vitro may range between about $10^{-5}$ molar and $10^{-9}$ molar concentrations. The dosage in vivo may range between about 0.001 and 25 mg/kg/day, preferably between about 0.0025 and 10 mg/kg/day depending on the compound and the route of administration.

Adenosine-2 (A-2) receptor binding properties, indicative of the adenosine-2 receptor agonist activity of the compounds of the invention are determined in vitro by determining their ability to inhibit the specific binding of $^3$H-5'-N-ethylcarboxamidoadenosine ($^3$H-NECA), e.g. essentially as described by R. F. Bruns et al, Mol. Pharmacol. 29, 331 (1986), in striatal membrane preparations from corpus striatum of male Sprague-Dawley rats. The concentration of a particular compound required to displace the specific binding of 4 nM $^3$H-NECA is determined in the presence of 50 nM cyclopentyladenosine.

Adenosine-1 (A-1) receptor binding properties of the compounds of the invention indicative of adenosine-1-receptor agonist activity are determined, e.g., essentially according to R. F. Bruns et al in Proc. Natl. Acad. Sci. U.S.A. 77:5547 (1980), by determining their ability to inhibit the specific binding of $^3$H-cyclohexyladenosine ($^3$H-CHA) in rat brain membrane preparations from male Sprague-Dawley rats. The concentration of a particular compound required to displace the specific binding of 1 nM $^3$H-CHA is determined.

Selectivity for the adenosine-2 (A-2) receptor can be ascertained by comparing the relative potency in the two adenosine receptor assays.

Indicative of in vivo adenosine-2 agonist activity, the hypotensive activity of the compounds of the invention as well as their effect on heart rate can be measured in normotensive or spontaneous hypertensive rats on intravenous or oral administration.

The blood pressure lowering effect on intravenous administration is preferably determined in the normotensive rat.

Hypotensive activity in the spontaneous hypertensive rat is determined as known in the art, preferably on oral administration.

Antithrombotic activity can be demonstrated by measuring the inhibition of collagen-induced platelet aggregation.

The compounds of the invention are selective adenosine-2 agonists and effectively lower blood pressure without any significant effect on the heart rate.

The compounds of the invention demonstrate an IC$_{50}$ as low as about $5 \times 10^{-8}$M in the in vitro adenosine-2-receptor binding assay and lower blood pressure in the spontaneous hypertensive rat at a dose as low as about 1 mg/kg p.o. They also demonstrate in vitro activity indicative of up to about 100 fold greater potency at the A-2 receptor than at the A-1 receptor. Illustrative thereof is 2-(2-cyclohexylethylamino)-adenosine.

The compounds of the invention, i.e. of formula I and herein cited derivatives thereof, are preferably prepared by a process which comprises condensing a compound of the formula V

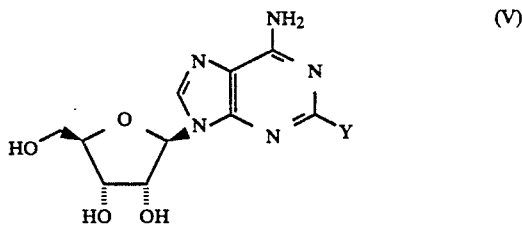

wherein Y represents a leaving group, with an amine of the formula VI

wherein $R_1$, $R_2$, $R_3$ and $R_4$ have meaning as defined hereinabove, or with an amine of the formula VIa

wherein $R_b$, t and $R_2$ have meaning as defined hereinabove, or with an amine of the formula VII

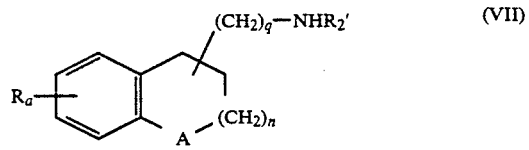

wherein A, n, q, $R_a$ and $R_2'$ have meaning as defined hereinabove; and, as required, temporarily protecting any interfering reactive group(s) in the starting materials and then subsequently removing the protecting groups to yield a resulting compound of formula I; and, if desired, converting a resulting compound of formula I into another compound of the invention, and if desired, converting a resulting free compound into a salt or a resulting salt into a free compound or into another salt, and if required, separating any mixture of diastereoisomers obtained into the single isomers.

A leaving group in the above process is nucleophilic and represents especially halo, for example chloro, bromo or iodo, aliphatically or aromatically substituted sulfonyloxy, for example methylsulfonyloxy or 4-methylphenylsulfonyloxy (tosyloxy), or aliphatically substituted thio, for example lower alkylthio such as methylthio.

In the preparation of the pharmaceutically acceptable esters of carboxylic acids cited herein, reactive functional derivatives of the carboxylic acids are used and such represent, for example, anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

In starting compounds and intermediates which are converted to the compounds of the invention in a manner described herein, functional groups present, such as amino and hydroxy, are optionally protected by conventional protecting groups that are common in preparative organic chemistry. Protected amino and hydroxy groups are those that can be converted under mild conditions into free amino and hydroxy groups without the molecular framework being destroyed or undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Greene, and "Protective Groups in Organic Synthesis", Wiley, New York 1984.

For example, a hydroxy group may be protected in the form of esters, e.g. as acyl derivatives such as the lower alkanoyl, benzoyl, benzyloxycarbonyl or lower alkoxycarbonyl derivative, or such hydroxy group may be protected in the form of ethers, e.g. as the lower alkyl, 2-tetrahydropyranyl, trityl or benzyl derivative.

Hydroxy groups on adjacent carbon atoms can also be protected e.g. in the form of ketals or acetals, such as lower alkylidene e.g. isopropylidene, benzylidene or 5- or 6-membered cycloalkylidene e.g. cyclopentylidene or cyclohexylidene derivatives.

In a resulting protected compound of formula I or intermediate, in which one or more of the functional groups are protected, the protected functional groups, e.g. hydroxy groups, can be liberated in a manner known per se, e.g. by means of solvolysis, especially hydrolysis with acid, or by hydrogenolysis.

The preparation of the compounds of the invention which involves the displacement of a leaving group Y (e.g. chloro) in a compound of the formula V or a protected derivative thereof by an amine of the formula VI VIa or VII is preferably carried out at elevated temperature, e.g. at a temperature ranging from about 75° to 150° C., with an excess of the amine, in the absence or presence of a solvent, particularly a polar solvent such as dimethylformamide or isoamyl alcohol, or under elevated pressure, optionally in the presence of a base such as a tertiary amine, e.g. triethylamine, or e.g. potassium carbonate.

The starting materials of formula V, e.g. 2-chloroadenosine, are known in the art.

The starting materials of formula VI, VIa and VII are either known in the art, or are prepared using methods known in the art, and/or as described and exemplified herein.

The compounds of the invention or intermediates leading thereto can be converted into other compounds of the invention or corresponding intermediates using chemical methodology known in the art, and as illustrated herein.

The conversion of compounds of formula I containing free hydroxy groups to ester derivatives thereof may be carried out by condensation with a corresponding carboxylic acid, advantageously as a reactive functional derivative thereof, according to acylation (esterification) procedures well-known in the art. For example, an appropriate carboxylic acid anhydride such as acetic anhydride is condensed with a compound of formula I in the presence of a suitable base, e.g. pyridine, triethylamine, 4-(dimethylamino)-pyridine, in an inert solvent such as acetonitrile.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures preferably near the boiling point for the solvents used, and at atmospheric or superatmospheric pressure.

The invention further includes any variant of the present processes, in which an intermediate product obtainable at any stage thereof is used as starting material and the remaining steps are carried out, or in which the starting materials are formed under the reaction conditions, or in which the reaction components are used in the form of their salts or optically pure antipodes. Whenever desirable, the above processes are carried out after first suitably protecting any potentially interfering reactive functional groups, as illustrated herein.

Advantageously, those starting materials should be used in said reactions that lead to the formation of those compounds indicated above as being preferred.

The invention also relates to novel starting materials and processes for their manufacture.

Depending on the choice of starting materials and methods, the new compounds may be in the form of isomers, for example, as diastereomers, as optical isomers (antipodes), or as mixtures thereof.

In case diastereomeric mixtures of the above compounds or intermediates are obtained, these can be separated into the single racemic or optically active isomers by methods in themselves known, e.g. by fractional distillation, crystallization or chromatography.

Any racemic intermediates can be resolved into the optical antipodes, for example, by separation of diastereomeric salts formed from optically active acids or bases.

Any basic intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Advantageously, the more active of the antipodes of the compounds of this invention is isolated.

Finally, the compounds of the invention are either obtained in the free form, or as a salt thereof. For example, any resulting free base can be converted into a corresponding acid addition salt, preferably with the use of a pharmaceutically acceptable acid or anion exchange preparation, or resulting salts can be converted into the corresponding free bases, for example, with the use of a stronger base, such as a metal or ammonium hydroxide, or any basic salt, e.g., an alkali metal hydroxide or carbonate, or a cation exchange preparation. These or other salts, for example, the picrates, can also be used for purification of the bases obtained; the bases are then first converted into salts. In view of the close relationship between the free compounds and the compounds in the form of their salts, whenever a compound is referred to in this context, a corresponding salt is also intended, provided such is possible or appropriate under the circumstances.

The compounds, including their salts, may also be obtained in the form of their hydrates, or include other solvents used for the crystallization.

The present invention also relates to the use of the compounds of the invention for the preparation of pharmaceutical compositions, especially pharmaceutical compositions having selective adenosine-2 agonist activity which can be used for the treatment of e.g. cardiovascular conditions, such as hypertension, thrombosis and atherosclerosis.

The pharmaceutical compositions according to the invention are those suitable for enteral, such as oral or rectal, transdermal and parenteral administration to mammals, including man, for the treatment of diseases responsive to adenosine-2 agonist activity, such as hypertension, comprising an effective adenosine-2 stimulating amount of a compound of the invention, alone or in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethylene glycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention also relates to the use of compounds of the invention having adenosine-2 agonist properties and pharmaceutical compositions comprising said compounds for the treatment in mammals of disorders responsive to selective adenosine-2 agonist activity particularly cardiovascular conditions (e.g. hypertension and thrombosis).

One aspect relates advantageously to a method of selectively enhancing adenosine-2 agonist activity in mammals and to the method of treating cardiovascular disorders in mammals, e.g. such responsive to adenosine-2 agonist activity, for example hypertension or thrombosis, using an effective amount of a compound of the invention, preferably in the form of the above-cited pharmaceutical compositions.

The dosage of active compound administered is dependent on the species of warm-blooded animal (mammal), the body weight, age and individual condition, and on the form of administration.

A unit dosage for a mammal of about 50 to 70 kg may contain between about 5 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, e.g. microanalysis and spectroscopic characteristics (e.g. MS, IR, NMR).

The numbering of the positions of the adenine or purine ring system is as conventionally used in the art (e.g. Merck Index, tenth edition).

EXAMPLE 1 a) A mixture of 1.65 g of 2-chloroadenosine and 3.7 g of p-(2-t-butoxycarbonyl-ethyl)-2-phenethylamine is heated at 130° for 3 hours. The reaction mixture is diluted with ethyl acetate and washed with saturated sodium bicarbonate solution. After drying over magnesium sulfate the solvent is removed in vacuo and the residue is chromatographed on silica gel with 10:1 methylene chloride/methanol saturated with ammonia as the eluent. The resulting product is triturated with ether to afford 2-[p-(2-t-butoxycarbonylethyl)-2-phenethylamino]-adenosine melting at 133°–137°.

The starting material is prepared as follows:

A mixture of 5 g of p-bromophenylacetonitrile, 4.6 ml of t-butyl acrylate, 57 mg of palladium diacetate, 310 mg of tri-o-tolylphosphine and 12 ml of triethylamine is refluxed for 5 hours. The reaction mixture is diluted with ethyl acetate and washed with 10% HCl and saturated sodium bicarbonate solution. After drying over magnesium sulfate the solvent is removed in vacuo. This material is dissolved in ethanol and hydrogenated over 1.1 g of 10% palladium on carbon catalyst for 3 days at 3 atmospheres pressure of hydrogen. After filtration the solvent is removed in vacuo and the residue is chromatographed on silica gel with ether/hexane (1:1) as the eluent to afford p-(2-t-butoxycarbonyl-ethyl)-phenylacetonitrile; 2.8 g of this product is dissolved in 90 ml of tetrahydrofuran and 50 ml of methanol and to this is added 6.2 g of cobalt chloride in 90 ml of water followed by 2.1 g of sodium borohydride in small portions. After filtration and removal of solvent, the residue is chromatographed on silica gel with 7.5% methanol saturated with ammonia in methylene chloride as the eluent to afford p-(2-t-butoxycarbonyl-ethyl)-2-phenethylamine as an oil.

b) 2-[p-(t-butoxycarbonylmethoxy)-2-phenethylamino]-adenosine is similarly prepared.

The starting material is prepared as follows:

A mixture of 3 g of p-hydroxyphenylacetonitrile, 3.6 ml of t-butyl bromoacetate, 6.5 g of potassium carbonate in 45 ml of dimethylformamide is stirred at room temperature for 16 hours. After dilution with water the product is extracted with ether. The ether layer is washed with 1 N sodium hydroxide, dried over magnesium sulfate and the solvent removed in vacuo to yield p-(t-butoxycarbonylmethoxy)-phenylacetonitrile which is reduced to p-(t-butoxycarbonylmethoxy)-2-phenethylamine with sodium borohydride/cobalt chloride as described for the starting material under a).

c) 2-[p-t-butoxycarbonylmethyl)-2-phenethylamino]-adenosine melting at 143°–146°.

The starting material is prepared as follows:

A mixture of 20 g of p-bromophenylacetic acid, 30 ml of ether, 1 ml of sulfuric acid and 35 ml of isobutylene is shaken in a sealed bottle for 24 hours. The reaction mixture is diluted with ether and washed with sodium hydroxide solution. After drying over magnesium sulfate the ether is removed in vacuo to afford the t-butyl ester as an oil. A mixture of 9.6 g of this material is refluxed with a mixture of 6.1 g of N-vinylphthalimide, 160 mg of palladium acetate, 800 mg of tri-o-tolylphosphine, 10 ml of acetonitrile and 8 ml of diisopropylethylamine for 24 hours. The reaction is diluted with water, the resulting precipitate is collected and recrystallized from methanol/methylene chloride. The resulting solid is hydrogenated at 4 atmospheres pressure over 2 g of 10% palladium on carbon catalyst in 100 ml of ethanol and 100 ml of tetrahydrofuran for 16 hours at room temperature. After removal of the solvent in vacuo the residue is heated at reflux with 10 ml of hydrazine hydrate and 20 ml of ethanol for 2 hours. The reaction is diluted with ether and washed with 5% potassium hydroxide solution. The ether solution is dried over magnesium sulfate and the solvent is removed in vacuo. The residue is chromatographed on silica gel, with 5% ammonia saturated methanol in methylene chloride as the eluent, to afford p-(t-butoxycarbonylmethyl)-2-phenethylamine as an oil.

d) 2-[p-(dimethylaminocarbonylmethyl)-2-phenethylamino]-adenosine, melting at 118°–121°, is similarly prepared.

The starting material is prepared as follows:

A mixture of 6 g of p-bromophenylacetic acid in 100 ml of methylene chloride and 5 ml of oxalyl chloride is stirred at room temperature for 16 hours. After removal of the solvent in vacuo the residue is dissolved in methylene chloride and treated with excess dimethylamine at room temperature. After 1 hour the reaction mixture is washed with water, the organic layer is dried over magnesium sulfate and the solvent is removed in vacuo to afford p-bromo-N,N-dimethyl-phenylacetamide as an oil, which is converted to p-(dimethylaminocarbonylmethyl)-2-phenethylamine as described for the starting material under c).

EXAMPLE 2 a) A mixture of 1.3 g of 2-[p-(2-t-butoxycarbonylethyl)-2-phenethylamino]-adenosine, 12 ml of 10% sodium hydroxide, 10 ml of methanol and 5 ml of tetrahydrofuran is heated at 50° for 2 hours. Acidification with 6N hydrochloric acid affords a solid which is collected and washed with a small volume of water to give 2-[p-(2-carboxyethyl)-2-phenethylamino]-adenosine hydrochloride melting at 170°–174°.

b) 2-[p-(carboxymethoxy)-2-phenethylamino]-adenosine hydrochloride, melting at 163°–167°, is similarly prepared.

EXAMPLE 3 a) A mixture of 1.0 g of 2-chloroadenosine, 1.2 g of 2-indanylamine, and 1.6 ml of diisopropylethylamine and 1.0 ml of isoamyl alcohol is refluxed for 16 hours. The reaction mixture is diluted with ethyl acetate and washed with saturated sodium bicarbonate solution. After drying over magnesium sulfate the solvent is removed in vacuo and the residue is chromatographed on silica gel with 10:1 methylene chloride/ammonia saturated methanol as the eluent. The resulting product is recrystallized from methanol to afford 2-(2-indanylamino)-adenosine melting at 129°–132°.

Similarly prepared are:

b) 2-(3,4-dihydro-6-fluoro-2H-[1]-benzothiopyran-3-ylamino)-adenosine melting at 125°–130°;

c) 2-(3,4-dihydro-6-bromo-2H-[1]-benzothiopyran-3-ylamino)-adenosine melting at 150°–154°;

d) 2-(3,4-dihydro-8-methoxy-2H-[1]-benzothiopyran-3-ylamino)-adenosine melting at 146°–150°;

e) 2-(3,4-dihydro-6-methoxy-2H-[1]-benzothiopyran-3-ylamino)-adenosine melting at 132°–135°;

f) 2-(3,4-dihydro-5-methoxy-2H-[1]-benzothiopyran-3-ylamino)-adenosine melting at 150°–153°;

The 3,4-dihydro-2H[1]-benzothiopyran-3-amine starting materials are prepared as illustrated for the starting material for the compound of Example 3 f) above.

To a cooled mixture of 30.6 g of m-methoxybenzenethiol, 54.4 g of 45% potassium hydroxide in 100 ml of dimethylsulfoxide is added 36.0 g of alpha-(bromomethyl)-acrylic acid in 25 ml of dimethylsulfoxide at such a rate as to maintain the reaction temperature at 50°–55°. After 1 hour the reaction mixture is diluted with water and washed with ether. After acidification, the product is extracted with ether, the organic layer is dried over magnesium sulfate and the solvent is removed in vacuo to afford alpha-(3-methoxybenzenethiomethyl)acrylic acid. This material is dissolved in 570 ml of o-dichlorobenzene and 7.2 g of triethylamine and heated to 200° for 5 hours. After cooling, the products are extracted with sodium bicarbonate solution, the aqueous layer is acidified and the products extracted with ether. After drying over magnesium sulfate, the solvent is removed in vacuo to afford a mixture of 3,4-dihydro-5-methoxy-2H-[1]-benzothiopyran-3-carboxylic acid and 3,4-dihydro-7-methoxy-2H-[1]-benzothiopyran-3-carboxylic acid.

This mixture of acids is dissolved in 500 ml of t-butyl alcohol and treated with 17 g of triethylamine and 36 ml of diphenylphosphoryl azide. After 5 hours reflux, the solvent is removed in vacuo and the residue is dissolved in ether and washed with 1 N sodium hydroxide and 1 N hydrochloric acid. After drying over magnesium sulfate, the solvent is removed in vacuo and the residue is chromatographed on silica gel (1 kg) with ether/hexane (1:4) as the eluent to afford in succession N-t-butoxycarbonyl-3,4-dihydro-5-methoxy-2H-[1]-benzothiopyran-3-amine and N-t-butoxycarbonyl-3,4-dihydro-7-methoxy-2H-[1]-benzothiopyran-3-amine.

A solution of 10 g of N-t-butoxycarbonyl-3,4-dihydro-5-methoxy-2H-[1]-benzothiopyran-3-amine in 30 ml of trifluoroacetic acid is kept at room temperature for 1 hour. The solvent is removed in vacuo, the residue is treated with 1 N NaOH and the product is extracted with ether. After drying over magnesium sulfate, the solvent is removed in vacuo to afford 3,4-dihydro-5-methoxy-2H-[1]-benzothiopyran-3-amine as an oil.

g) 2-[3,4-dihydro-2H-[1]-benzopyran-3-ylamino]-adenosine;

h) 2-[1,2,3,4-tetrahydro-2-naphthylamino]-adenosine.

EXAMPLE 4

The following compounds are prepared according to procedures described in the previous examples.

a) 2-(p-carboxymethyl-2-phenethylamino)-adenosine melting at 150°–160°; hydrochloride salt, m.p. 132°–140°;

b) 2-[(p-diethylaminocarbonyl)-2-phenethylamino]-adenosine melting at 105°–108°;

c) 2-[p-(diethylaminocarbonylmethyl)-2-phenethylamino]adenosine melting at 89°–94°;

d) 2-[p-(2-dimethylaminocarbonylethyl)-2-phenethylamino]-adenosine, melting at 139°–143°;

e) 2-(p-carboxymethyl-2-phenylpropylamino)-adenosine;

f) 2-[p-(diethylaminocarbonylmethoxy)-2-phenethylamino]-adenosine.

g) 2-(2-phenylpropylamino)-adenosine, melting at 116°–119°; [alpha]$_D$ —21.1° (methanol);

h) 2-(S-2-phenylpropylamino)-adenosine, melting at 111°–115°; [alpha]$_D$ —68.3 (methanol); prepared from the levorotatory (S)-2-phenylpropylamine, J. Med. Chem. 17, 717 (1974);

i) 2-(N-methyl-2-phenethylamino)-adenosine, melting at 82°–94°; prepared from N-methylphenethylamine;

j) 2-[N-methyl-2-(2-pyridyl)-ethylamino]-adenosine;

k) 2-[N-methyl-2-(2-thienyl)-ethylamino]-adenosine;

l) 2-[N-methyl-9H-fluorenyl-methylamino]-adenosine;

m) 2-[2-(2-pyridyl)-propylamino]-adenosine;

n) 2-[2-(2-pyridyl)ethylamino]-adenosine, melting at 177°–180° C.; [alpha]$_D$ —29.7° (dimethylsulfoxide);

o) 2-[2-(3-indolyl)-ethylamino]-adenosine; melting at 125°–141°, [alpha]$_D$ —25.8° (methanol);

p) 2-[(9-9H-fluorenyl)-methylamino]-adenosine.

q) 2-(2-cyclohexylethylamino)-adenosine, melting at 142°–145°.

r) 2-[(S)-N-methyl-2-phenylpropylamino]-adenosine hydrochloride, [alpha]$_D$ —56.8° (methanol);

s) 2-[(S)-N-ethyl-2-phenylpropylamino]-adenosine hydrochloride, [alpha]$_D$ —70.0° (methanol);

t) 2-[2-(p-t-butoxycarbonylphenyl)ethyl amino]-adenosine, melting at 155°–160°;

u) 2-(2-cyclopentylethylamino)-adenosine, melting at 124°–131°;

v) 2-[2-[p-(2-t-butoxycarbonylethyl)-phenyl]-N-methyl-ethylamino]-adenosine, melting at 76°–78°;

w) 2-[2-(p-carboxyphenyl)-ethylamino]-adenosine, dihydrochloride melting at 165°–170°;

x) 2-[2-(1-carboxymethyl-3-indolyl)-ethylamino]-adenosine.

y) 2-[2-(1-tert-butoxycarbonylmethyl-3-indolyl)-ethylamino]-adenosine, melting at 105°–120°.

EXAMPLE 5

Condensation of 2-(4-bromo-2-thienyl)-ethylamine with 2-chloroadenosine essentially according to the procedure in the previous examples yields 2-[2-(4-bromo-2-thienyl)-ethylamino]-adenosine, melting at 136°–144°.

The starting 2-(4-bromo-2-thienyl)ethylamine is prepared in the following way:

A mixture of 4-bromothiophene-2-carboxaldehyde (95.5 g), nitromethane (32 g) and methanol (600 ml) chilled in an ice-bath at 0°–5° is gradually treated with 10N sodium hydroxide (55 ml). It is then stirred 5 minutes at 0°–5°, warmed to room temperature over 30 minutes, and added gradually to ice-cold 6N hydrochloric acid (120 ml). The precipitated product, 4-bromo-2-(β-nitrovinyl)-thiophene, is washed throughly with water and vacuum oven dried at 50° over 18 hours to afford pure 4-bromo-2-(β-nitrovinyl)thiophene, melting at 107°–110°. The nitro compound (35.1 g) in dry ether (1500 ml) is added slowly to a chilled suspension of lithium aluminum hydride (12.5 g) in ether (150ml) and stirring is continued overnight at room temperature. The mixture is treated with water (12.5 ml), followed by 15% sodium hydroxide solution (12.5 ml) and again water (37.5 ml) under ice cooling, stirred 30 minutes and filtered; the ethereal layer is then treated with 3N hydrochloric acid. The aqueous solution is then made basic with 10N sodium hydroxide and ice, and the amine is extracted with ether. The dried (Na$_2$SO$_4$) ethereal solution is concentrated to dryness at reduced pressure to give the 2-(4-bromo-2-thienyl)-ethylamine.

EXAMPLE 6

A mixture of 2-chloroadenosine (300 mg) and β-hydroxyphenethylamine (700 mg) is heated under nitrogen in an oil bath at 130° for 2.5 hours. It is cooled and separated between ethyl acetate and 5% sodium bicarbonate solution. The organic layer is washed with brine, dried over sodium sulphate and concentrated to dryness. The resulting solid is triturated with methylene chloride over 15 minutes and collected to afford 2-(2-hydroxy-2-phenethylamino)-adenosine, melting at 114°–125°.

EXAMPLE 7 a) A mixture of 2-chloroadenosine (0.3 g), p-benzyloxy-β-hydroxy-β-methyl-2-phenethylamine hydrochloride (0.88 g), diisopropylethylamine (1.3 g) and isoamyl alcohol (5ml) is heated under nitrogen at reflux over 74 hours. It is concentrated to dryness at reduced pressure and flash chromatographed through silica gel with 9:1 methylene chloride: ammonia-saturated methanol as eluent. The major product is collected, triturated with ether and dried at reduced pressure to afford 2-(p-benzyloxy-2-hydroxy-2-methyl-2-phenethylamino)-adenosine, melting at 113°–122°.

b) Similarly prepared is 2-(2-hydroxy-2-methyl-2-phenethylamino)-adenosine, [alpha]$_D$—20.1° (methanol).

EXAMPLE 8 a) A mixture of 2-chloroadenosine (3 g) and 2-(4-β-tert-butoxycarbonylvinyl-2-thienyl)-ethylamine (11.4 g) is heated under nitrogen at 140° over 6 hours. It is cooled, the residue is dissolved in ethyl acetate, the solution is washed with saturated sodium bicarbonate solution, dried over sodium sulphate and concentrated to dryness at reduced pressure. The residue is chromatographed over silica gel with 19:1 methylene chloride: methanol saturated with ammonia as eluent followed by a 5:1 mixture of the same solvents. The fractions containing the desired product are combined and concentrated to dryness. The residue is triturated with ether to afford 2-[2-(4-β-tert-butoxycarbonylvinyl-2-thienyl)-ethylamino]-adenosine, [alpha]$_D$—18.7° (methanol).

The starting material is prepared from 2-(4-bromo-2-thienyl)-ethylamine (example 5) in the following way:

A mixture of 2(4-bromo-2-thienyl)-ethylamine (37 g) and phthalic anhydride (26.7 g) in glacial acetic acid (500 ml) is heated at reflux over 15 hours. It is concentrated at reduced pressure, the residue is triturated with ethanol and collected. The solid is recrystallized from ethanol to afford N-[2-(4-bromo-2-thienyl)ethyl]-phthalimide, m.p. 115°–117°.

A mixture of the above phthalimide (28.2 g), tertbutyl acrylate (14.2 g), palladium acetate (0.19 g), tri-o-tolylphosphine (1.02 g) and triethylamine (56 g) is stirred under nitrogen at an oil bath temperature of 140° over 18 hours. The mixture is poured into cold dilute hydrochloric acid and extracted with ethyl acetate. The extract is washed with saturated sodium chloride, dried over sodium sulphate, decolorized with charcoal and concentrated to yield N-[2-(4-β-tert-butoxycarbonylvinyl-2-thienyl)-ethyl]-phthalimide.

A mixture of the above phthalimide (29.8 g), hydrazine hydrate (7.6 ml) and ethanol (500 ml) is heated at reflux for 6 hours. The mixture is concentrated to dryness at reduced pressure, treated with 10% aqueous potassium hydroxide and extracted with ether. The ether layer is washed with brine, dried over sodium sulphate, decolorized with charcoal and concentrated to dryness. The resulting oil is chromatographed through silica gel with 19:1 methylene chloride: methanol saturated with ammonia as eluent. Combination of the desired fractions gives 2-(4-β-tert-butoxycarbonylvinyl-2-thienyl)-ethylamine as a pale yellow oil.

b) 2-[2-(4-tert-butoxycarbonylethyl-2-thienyl)-ethylamino]-adenosine melting at 120°–124° is prepared similarly.

The starting material is prepared as follows:

A mixture of N-[2-(4-β-tert-butoxycarbonylvinyl-2-thienyl)-ethyl]-phthalimide (10 g) and ethanol (200 ml) with 10% palladium on carbon (5 g) is hydrogenated at 3 atmospheres pressure and at 25° over 12 hours. The mixture is filtered and concentrated to dryness at reduced pressure to afford a pale yellow oil. The oil is combined with ethanol (100 ml) and hydrazine hydrate (2.0 ml) and the mixture is heated under reflux for 6 hours. It is concentrated to dryness at reduced pressure, treated with 10% aqueous potassium hydroxide and extracted with ether. The ether extract is dried over sodium sulphate and concentrated to dryness to give 2-(4-β-tert-butoxycarbonylethyl-2-thienyl)-ethylamine as an oil.

EXAMPLE 9 a) The product of Example 8(a) (0.41 g) is stirred at 65° in 1 N hydrochloric acid (5 ml) for 1 hour. The mixture is cooled and the solid collected, washed with water, then ether, triturated with isopropanol and dried to yield 2-[2-(4-β-carboxyvinyl-2-thienyl)ethylamino]-adenosine hydrochloride melting at 197°–204°.

b) Similarly prepared from the product of example 8(b) is 2-[4-(2-carboxyethyl)-2-thienyl)-ethylamino]-adenosine, melting at 199°–204°.

EXAMPLE 10

A mixture of 2-chloroadenosine (15.05 g) and 2-cyclohexylethylamine (31.75 g) is stirred under nitrogen at 140° over 6 hours. The reaction mixture is cooled to room temperature, diluted with ethanol (500 ml), propylene oxide (50 ml) is added and the mixture is stirred at room temperature for 3 hours. The solid is collected by vacuum filtration, washed with ethanol, then ether, and dried at 80°/0.1 mm over 16 hours. The white solid obtained is recrystallized from ethanol to yield 2-(2-cyclohexylethylamino)-adenosine, the compound of example 4q, m.p. 142°–145°, [alpha]$_D^{25}$ —30.5° (c=1, dimethyl sulfoxide).

EXAMPLE 11

A mixture of 2-chloroadenosine (0.3 g) and 2-(2-aminoethyl)-5-bromothiophene (2.1 g) is stirred under nitrogen at 140° C. over 18 hours. It is concentrated to a small volume under high vacuum (0.1 mm Hg) at 50° C., and the residue is purified by flash chromatography through a silica gel column (25×200 mm) eluting with methylene chloride/ammonia-saturated methanol (9:1). Fractions containing the major product are combined and concentrated to dryness at reduced pressure. The residue is recrystallized from methanol-ether and then from acetonitrile with charcoal to afford 2-[2-(5-bromo-2-thienyl)ethylamino]-adenosine, m.p. 145°–152° dec.

The starting 2-(2-aminoethyl)-5-bromothiophene is prepared in the following manner:

Sodium borohydride (18.1 g) is suspended in dry tetrahydrofuran (500 ml), chilled in an ice bath and treated slowly with boron trifluoride etherate. After the addition, the mixture is stirred at room temperature for 45 minutes and then a solution of 5-bromo-2-($\beta$-nitrovinyl)thiophene (23.4 g) in tetrahydrofuran (250 ml) is gradually added. The mixture is then stirred under reflux under nitrogen for 2 hours, cooled to room temperature and cautiously treated with water (250 ml) followed by 6N hydrochloric acid (250 ml). The mixture is heated under reflux for 2 hours, cooled and extracted with ether (3×250 ml). The aqueous layer is then made basic with cold sodium hydroxide and extracted with ether (2×250 ml). The ether extract is washed with brine, dried over sodium sulphate, decolorized with charcoal and evaporated to dryness at reduced pressure to yield 2-(5-bromo-2-thienyl)ethylamine as an oil; hydrochloride salt, crystallized from 2-propanol-ether, m.p. 215°–220° dec.

EXAMPLE 12

A mixture of 2-chloroadenosine (0.3 g), diisopropylethylamine (0.18 ml) 2-(1-adamantyl)ethylamine (0.18 ml) and isoamyl alcohol (5 ml) is stirred under nitrogen 18 hours at 140°. It is cooled, diluted with ether (25 ml), and stirred one hour. The solid is collected, triturated with water, filtered off and air dried. The material is recrystallized from dimethylformamide-ether, to afford 2-[2-(1-adamantyl)ethylamino]adenosine, m.p. 145°–7°.

EXAMPLE 13 a) A mixture of 2-chloroadenosine (0.30 g) and 2-(1-cyclohexenyl)-ethylamine (0.63 g) is stirred under nitrogen for 6 hours at 140° C. The solution is concentrated to dryness at reduced pressure; the residue is dissolved in ethanol, treated with propylene oxide (2 ml) and stirred at room temperature for 16 hours. The mixture is concentrated to dryness at reduced pressure and flash chromatographed through a 25×150 mm column of silica gel using methylene chloride and methanol saturated with ammonia (9:1) as eluent. Fractions containing the desired product are combined, concentrated to dryness at reduced pressure; the residue is redissolved in hot ethanol, the solution is decolorized with charcoal and then concentrated to dryness. The residual solid is triturated with ethanol (2 ml) and collected to afford 2-[2-(1-cyclohexenyl)-ethylamino]adenosine, m.p. 135°–38°.

b) Similarly prepared is 2-[2-(S-6,6-dimethylbicyclo-[3.1.1]hept-2-en-2-yl)ethylamino]-adenosine, by condensation of 2-chloroadenosine with 2-[(S)-6,6-dimethylbicyclo[3.1.1]hept-2-en-2-yl]ethylamine. The amine can be prepared by first converting the alcohol to the tosyl derivative which is then treated with hexamethylenetetramine and then hydrolysed to the amine hydrochloride with concentrated hydrochloric acid.

EXAMPLE 14

A mixture of 2-chloroadenosine (0.30 g) and 4-(2-aminoethyl)-stilbene (1.11 g) is stirred at 140° under nitrogen over 6 hours. It is cooled, diluted with ethanol (25 ml), treated with propylene oxide (5 ml) and stirred 1 hour at room temperature. It is filtered free of starting material and the filtrate is concentrated at reduced pressure and purified by flash chromatography through a 25×200 mm column of silica gel with $CH_2Cl_2$ and ammonia-saturated methanol (9:1) as eluent. Fractions containing the desired material are combined and evaporated at reduced pressure and the residual solid is recrystallized from acetonitrile with charcoal treatment. The product, 2-[2-(4-stilbenyl)ethylamino]-adenosine, $[alpha]_D^{25} = -28.6°$ in DMSO, has m.p. 165°–169°.

The starting amine is prepared in the following manner:

A mixture of 4-bromophenethylamine (30 g), phthalic anhydride (22.2 g) and glacial acetic acid (300 ml) is heated under reflux for 18 hours. The mixture is concentrated to dryness at reduced pressure, the residue is triturated and stirred 0.5 hour in ethanol (150 ml); the solid is collected, washed with ethanol and dried under vacuum to yield 4-bromophenethylphthalimide.

A mixture of 4-bromophenethylphthalimide (23.1 g), styrene (9.5 g), palladium acetate (0.16 g), tri-o-tolylphosphine (0.85 g) and triethylamine (46.5 g) is stirred at reflux under nitrogen for 18 hours. It is cooled, treated with ice cold dilute hydrochloric acid and extracted with ethyl acetate (3×500 ml). The ethyl acetate extract is washed with water, then brine, dried over sodium sulphate and concentrated to dryness at reduced pressure. Recrystallization from 2-methoxyethanol affords N-(4-stilbenylethyl)-phthalimide, m.p. 212°–215°.

The phthalimide (5.65 g) is combined with ethanol (100 ml) and hydrazine hydrate (1.6 g) and the mixture is heated 18 hours under reflux. The mixture is concentrated to dryness at reduced pressure, treated with ice-cold aqueous potassium hydroxide and extracted with ethyl acetate. The ethyl acetate extract is washed with water, then brine, dried over sodium sulphate and concentrated to dryness at reduced pressure to give 4-(2-aminoethyl)-stilbene, m.p. 141°–156°.

EXAMPLE 15

By reaction of 2-chloroadenosine with 2-[p-(phenylethyl)-phenyl]ethylamine in the manner described e.g. in Example 14, 2-[2-(p-phenylethyl-phenyl)-ethylamino]-adenosine, $[alpha]_D^{25} = -25.6°$ in DMSO, m.p. 148°–150°, is obtained.

The starting amine is prepared in the following way:

A mixture of 4-(2-aminoethyl)-stilbene (2.23 g), 10% palladium on charcoal (0.25 g), ethanol (200 ml) and 1N hydrochloric acid (20 ml) is hydrogenated at 3 atmospheres pressure over 3 hours. The mixture is filtered, the solid material is stirred with excess aqueous/ethanolic sodium hydroxide and the suspension refiltered. The filter cake is extracted with ethyl acetate several times and the organic extracts are washed with water, then brine and dried over sodium sulphate. Evaporation of the solvent yields 2-[4-phenylethyl)-phenyl]-ethylamine.

EXAMPLE 16

Reaction of 2-chloroadenosine with p-(cyclohexylvinyl)phenylethylamine in the manner described e.g. in Example 14 gives 2-[2-(p-cyclohexylvinyl-phenyl)-ethylamino]-adenosine, [alpha]$_D^{25}$ = −26.4° in DMSO, m.p. 161°–164°.

The starting amine is prepared from p-bromophenethylphthalimide and vinylcyclohexane (instead of styrene) by the sequence of reactions described for the starting amine in Example 14, via N-(p-cyclohexylvinylphenethyl)-phthalimide, m.p. 135°–138°.

EXAMPLE 17

Reaction of 2-chloroadenosine with p-(2-cyclohexylethyl)-phenethylamine as described in Example 14 gives 2-[2-(p-2-cyclohexylethyl-phenyl)-ethylamino]-adenosine, [alpha]$_D^{25}$ = −25.6° in DMSO, m.p. 154°–160°.

The starting amine is prepared in the following way:

The intermediate from Example 16, N-(p-cyclohexylvinylphenethyl)phthalimide (9.0 g) and 10% palladium on charcoal (0.9 g) in ethyl acetate (700 ml) is shaken with hydrogen at 3 atmospheres pressure over 7 hours. The mixture is filtered and the filtrate concentrated to dryness at reduced pressure to give N-[p-(2-cyclohexylethyl]-phenethyl]-phthalimide, m.p. 135°–138° after recrystallization from ethanol. The phthalimide (5.75 g) is added to a mixture of hydrazine hydrate (1.6 g) in methanol (100 ml) and heated under reflux for 18 hours. The mixture is concentrated to dryness at reduced pressure, made basic with cold concentrated aqueous potassium hydroxide and extracted with ethyl acetate. The organic extract is washed with water, then brine, dried over sodium sulphate and concentrated to dryness at reduced pressure to give the desired amine as an oil which gradually solidifies on standing.

EXAMPLE 18

The reaction of 2-chloroadenosine with t-butyl 3-[4-(2-aminoethyl)-cyclohexyl]-propionate according to the procedure described in Example 14 yields 2-{2-[4-(2-t-butyoxycarbonyl-ethyl)-cyclohexyl]-ethylamino}-adenosine, [alpha]$_D^{25}$ = −22.3° in methanol, m.p. 118°–122°.

The starting amine is prepared in the following way:

The hydrochloride salt of p-(2-t-butoxycarbonylethyl)-2-phenethylamine, the intermediate of Example 1a, (4.7 g), is hydrogenated in glacial acetic acid (200 ml) with platinum oxide (0.5 g) at 3 atmospheres pressure over 14 hours. The catalyst is filtered off and the filtrate concentrated to dryness at reduced pressure. The residue is made basic with ice cold sodium hydroxide solution and extracted several times with ether. The ether extract is washed with brine, dried over sodium sulphate and concentrated to dryness at reduced pressure. The residual solid is shown by proton and carbon N.M.R. to be a mixture of cis and trans t-butyl 3-[4-(2-aminoethyl)-cyclohexyl]-propionate.

EXAMPLE 19

The ester from Example 18 (0.31 g) is stirred in trifluoroacetic acid at room temperature for 1 hour, the mixture is concentrated to dryness at reduced pressure, the residue is triturated with dry ether (20 ml) and the suspension is stirred overnight. The solid is collected and dried under vacuum to afford 2-{2-[4-(2-carboxyethyl)-cyclohexyl]ethylamino}-adenosine trifluoroacetate, [alpha]$_D^{25}$ = −11.5° in DMSO, m.p. 105°–125°.

EXAMPLE 20

A mixture of 2-chloroadenosine (0.3 g) and 1,4-dioxaspiro[4.5]decane-8-ethanamine (1.0 g) is heated under nitrogen at 140° for 6 hours. It is evaporated to dryness at reduced pressure, the residue is dissolved in ethanol, the solution is treated with propylene oxide (2 ml) and stirred 4 hours. The precipitate is collected, washed with ethanol and dried in vacuo to give 2-[2-(1,4-dioxaspiro[4.5]dec-8-yl)ethylamino]adenosine, [alpha]$_D^{25}$ = −27.3° (MeOH), m.p. 133°–137°.

The starting amine is prepared in the following manner:

To a suspension of sodium hydride (50% in mineral oil, 1.15 g, washed with hexane) in toluene (50 ml) is added a solution of diethyl cyanomethylphosphonate (4.25 g) in toluene (50 ml) dropwise under nitrogen and the mixture is stirred 30 minutes longer. A solution of 1,4-cyclohexanedione monoethylene ketal (3.12 g) in toluene (50 ml) is added dropwise under nitrogen at room temperature. After 10 minutes, ice water is added under vigorous stirring. The aqueous layer is collected and extracted several times with ether. The combined toluene-ether extracts are washed with water, then brine, dried over sodium sulphate and concentrated to dryness at reduced pressure. The residual oil is chromatographed through a 25×140 mm column of silica gel, using methylene chloride as solvent to afford an oil which gradually crystallizes to give 8-cyanomethylene-1,4-dioxaspiro[4.5]decane.

The above nitrile (2.15 g) is treated with platinum oxide (0.1 g) in ethanol (200 ml) and hydrogenated at 3 atmospheres pressure over 4 hours. Removal of the catalyst and concentration of the solvent gives 8-cyanomethyl-1,4-dioxaspiro[4.5]decane as an oil.

The nitrile (2.0 g) in ether (100 ml) is added slowly to an ice-cold mixture of lithium aluminum hydride (0.6 g) in ether (25 ml) and the mixture is stirred for 2 hours at ice-bath temperature. The resulting mixture is treated with water (0.6 ml), 15% sodium hydroxide solution (0.6 ml) and again water (1.8 ml). The suspension is filtered and the filtrate is concentrated to dryness at reduced pressure to give 1,4-dioxaspiro[4.5]decane-8-ethanamine as an oil.

EXAMPLE 21

A mixture of 2-chloroadenosine (0.3 g) and 2-(tetrahydropyran-4-yl)ethylamine (1.15 g) is stirred under nitrogen at 140° for 6 hours. The mixture is concentrated to dryness at reduced pressure, the residue is dissolved in ethanol, the solution is treated with propylene oxide (2 ml) and stirred overnight. It is concentrated to dryness and chromatographed through a 25×180 mm column of silica gel, with methylene chloride and ammonia-saturated methanol (9:1) as eluent. The fractions containing the desired product are combined and concentrated at reduced pressure. The residue is dissolved in absolute ethanol and treated with ethanolic hydrogen chloride to form the hydrochloride salt of 2-[2-(tetrahydropyran-4-yl)ethyl-amino]adenosine; [alpha]$_D^{25}$ −13.6° (DMSO); m.p. 120°–130° dec.

The starting amine is prepared in the following manner:

A mixture of tetrahydropyran-4-one (12 g), ethyl cyanoacetate (13.6 g), ammonium acetate (1.2 g), glacial acetic acid (2.4 ml) and toluene (15 ml) is stirred at reflux for 16 hours. The mixture is diluted with toluene and the organic layer is separated, washed with water, then brine, and dried over magnesium sulfate. It is concentrated at reduced pressure to an oil which solidifies. It is further purified by flash chromatography through silica gel with methylene chloride as eluent. The desired fractions are combined and concentrated to dryness at reduced pressure to afford 4-(alpha-ethoxycarbonyl-cyanomethylene)-tetrahydropyran.

The unsaturated cyano ester obtained above (13 g) is dissolved in ethanol (700 ml), treated with platinum oxide (0.65 g) and hydrogenated at 3 atmospheres pressure over 70 minutes. The catalyst is filtered off and the solution concentrated in vacuo to afford ethyl alpha-(tetrahydro-pyran-4-yl)-cyanoacetate.

A mixture of the above cyanoacetate (12.5 g), sodium chloride (1.5 g), water (1.5 ml) and dimethyl sulfoxide (75 ml) is heated in an oil bath at 150° over 8 hours. The mixture is concentrated under vacuum and the residue diluted with water and extracted with ether. The ether extract is washed with water, then brine, decolorized with charcoal, dried over sodium sulphate and concentrated to an oil, 4-cyanomethyl tetrahydropyran.

This nitrile (4.2 g) in ether (200 ml) is added slowly to a suspension of lithium aluminum hydride (2.0 g) in ether (100 ml) at 0° C. It is stirred 18 hours at ambient temperature, then treated with water (2 ml), 15% aqueous sodium hydroxide (2 ml) and again water (6 ml). It is filtered and the filtrate extracted with 3N hydrochloric acid. The acidic extract is washed with ether, then made basic with cold aqueous sodium hydroxide. The alkaline solution is extracted with ether and the dried ether extracts are concentrated to dryness at reduced pressure to afford oily 2-(tetrahydropyran-4-yl)ethylamine, suitable for the final step.

EXAMPLE 22

Prepared essentially according to procedures described in the previous examples are:
 (a) 2-(2-phenylcyclopropylamino)-adenosine, m.p. 134°–145°;
 (b) 2-(3-cyclohexylpropylamino)-adenosine;
 (c) 2-(6-cyclohexylhexylamino)-adenosine;
 (d) 2-[2-(2-norbornanyl)-ethylamino]-adenosine;
 (e) 2-[2-(tetrahydrothiopyran-4-yl)-ethylamino]-adenosine.

EXAMPLE 23 a) Preparation of 10,000 tablets each containing 10 mg of the active ingredient:

| Formula: | |
|---|---|
| 2-(2-cyclohexylethylamino)-adenosine | 100.00 g |
| Lactose | 2,400.00 g |
| Corn starch | 125.00 g |
| Polyethylene glycol 6,000 | 150.00 g |
| Magnesium stearate | 40.00 g |
| Purified water | q.s |

PROCEDURE

All the powders are passed through a screen with openings of 0.6 mm. Then the drug substance, lactose, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets, using concave punches uppers bisected.

b) Preparation of 1,000 capsules each containing 10 mg of the active ingredient:

| Formula: | |
|---|---|
| 2-[p-(2-carboxyethyl)-2-phenethylamino]-adenosine | 10.0 g |
| Lactose | 207.0 g |
| Modified starch | 80.0 g |
| Magnesium stearate | 3.0 g |

PROCEDURE

All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

What is claimed is:
1. A compound of the formula I

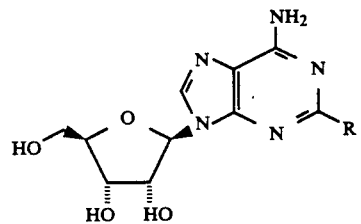

in which the substituent R represents

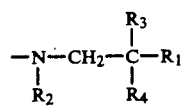

(a) wherein $R_1$ represents phenyl substituted by a substituent -W-Z in which W represents a direct bond, lower alkenylene, lower alkylene, thio-lower alkylene or oxy-lower alkylene and Z represents cyano, carboxy or carboxy derivatized in the form of a pharmaceutically acceptable ester or amide; $R_2$ represents hydrogen or lower alkyl; $R_3$ and $R_4$ independently represent hydrogen or lower alkyl; or (b) wherein $R_1$ represents phenyl substituted by one to three of lower alkyl, lower alkoxy, hydroxy, lower alkanoyloxy, halogen, benzyloxy or trifluoromethyl; $R_2$ represents hydrogen or lower alkyl; $R_3$ represent hydrogen, lower alkyl or hydroxy, and $R_4$ represents hydrogen or lower alkyl, with the proviso that $R_2$ does not represent hydrogen if both $R_3$ and $R_4$ represent hydrogen; or (c) wherein $R_1$ represents a heterocyclic aromatic radical selected from pyridyl, thienyl, pyrrolyl and indolyl, each optionally substituted by halogen, lower alkyl or -W-Z as defined under (a); $R_2$ represents hydrogen or lower alkyl; $R_3$ and $R_4$ independently represent hydrogen or lower alkyl; or (d) wherein $R_1$ represents $C_3$-$C_7$-cycloalkyl; $R_2$ represents hydrogen or lower alkyl; $R_3$ and $R_4$ independently represent hydrogen or lower alkyl; or (e) wherein the —$CR_1R_3R_4$ moiety as a single group represents 9-fluorenyl; $R_2$ represents hydrogen or lower alkyl; or (f) wherein $R_1$ represents either phenyl or $C_5$-$C_7$-cycloalkyl substituted by a substituent -W-Z in which W represents lower alkylene and Z represents hydroxy; $R_2$ represents hydrogen or lower alkyl; $R_3$ and $R_4$ independently represent hydrogen or lower alkyl; or (g) wherein $R_1$ represents phenyl substituted by -W-Z, in which W represents lower alkylene or lower alkenylene and Z represents phenyl or $C_5$-$C_7$ cycloalkyl; $R_2$ represents hydrogen or lower alkyl; $R_3$ and $R_4$ independently represent hydrogen or lower alkyl; or (h) wherein $R_1$ represents $C_5$-$C_7$-cycloalkyl substituted by a substituent-W-Z in which W represents a direct bond or lower alkylene and Z represents carboxy or carboxy derivatized in the form of a pharmaceutically acceptable ester or amide, or substituted by one or two of lower alkyl, hydroxy, lower alkanoyloxy or lower alkoxy, or substituted by lower alkylenedioxy in which the two oxygen atoms are attached to the same carbon atom or on adjacent carbon atoms; $R_2$ represents hydrogen or lower alkyl; $R_3$ and $R_4$ independently represent hydrogen or lower alkyl; or (i) wherein $R_1$ represents bicycloheptyl optionally substituted by lower alkyl, bicycloheptenyl optionally substituted by lower alkyl, or adamantyl; $R_2$ represents hydrogen or lower alkyl; $R_3$ and $R_4$ independently represent hydrogen or lower alkyl; or (j) wherein $R_1$ represents cyclohexenyl or cyclohexenyl substituted by lower alkyl; $R_2$ represents hydrogen or lower alkyl; $R_3$ and $R_4$ independently represent hydrogen or lower alkyl; or (k) wherein $R_1$ represents tetrahydropyranyl or tetrahydrothiopyranyl; $R_2$ represents hydrogen or lower alkyl; $R_3$ and $R_4$ independently represent hydrogen or lower alkyl;

or a compound of formula I in which the substituent R represents

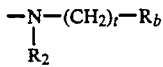

wherein $R_2$ represents hydrogen or lower alkyl; t represents the integer 3, 4, 5 or 6; and $R_b$ represents (a) $C_3$-$C_7$-cycloalkyl optionally substituted by lower alkyl;

(b) cyclohexenyl optionally substituted by lower alkyl;

(c) bicycloheptyl optionally substituted by lower alkyl;

(d) bicycloheptenyl optionally substituted by lower alkyl;

(e) a heterocyclic aromatic radical selected from pyridyl, thienyl, pyrrolyl and indolyl, each optionally substituted by lower alkyl or halogen; or (f) phenyl substituted by halogen, lower alkyl, lower alkoxy, trifluoromethyl, cyano, carboxy, lower alkoxycarbonyl, carbamoyl, N-mono- or N,N-di-lower alkylcarbamoyl;

or a compound of formula I in which the substituent R represents

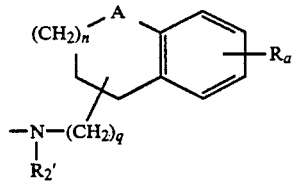

in which A represents methylene, oxy or thio, n represents zero or one, q represents zero, one or two, and $R_a$ represents hydrogen, lower alkyl, lower alkoxy, halogen or -W-Z in which W represents a direct bond, lower alkenylene, lower alkylene, thio-lower alkylene or oxy-lower alkylene, and Z represents cyano, carboxy, carboxy derivatized in the form of a pharmaceutically acceptable ester or carboxy derivatized in the form of a pharmaceutically acceptable amide; and $R_2'$ represents hydrogen or lower alkyl; or a pharmaceutically acceptable salt thereof;

wherein in the above definitions carboxy derivatized in the form of a pharmaceutically acceptable ester represents lower alkoxycarbonyl; carboxy derivatized in form of a pharmaceutically acceptable amide represents carbamoyl, mono-N-lower alkylcarbamoyl or N,N-di-lower alkylcarbamoyl.

2. A compound according to claim 1 of the formula II

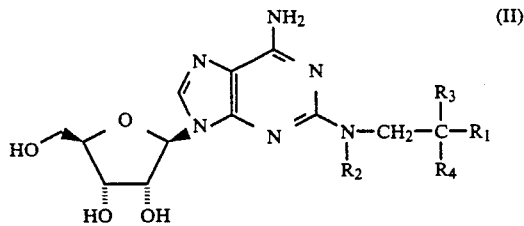

(a) wherein $R_1$ represents phenyl substituted by a substituent -W-Z in which W represents a direct bond, lower alkenylene, lower alkylene, thio-lower alkylene or oxy-lower alkylene and Z represents cyano, carboxy or carboxy derivatized in the form of a pharmaceutically acceptable ester or amide; $R_2$ represents hydrogen or lower alkyl; $R_3$ and $R_4$ independently represent hydrogen or lower alkyl; or (b) wherein $R_1$ represents phenyl substituted by one to three of lower alkyl, lower alkoxy, hydroxy, lower alkanoyloxy, halogen, benzyloxy or trifluoromethyl; $R_2$ represents hydrogen or lower alkyl; $R_3$ represent hydrogen, lower alkyl or hydroxy, and $R_4$ represents hydrogen or lower alkyl, with the proviso that $R_2$ does not represent hydrogen if both $R_3$ and $R_4$ represent hydrogen; or (c) wherein $R_1$ represents a heterocyclic aromatic radical selected from pyridyl, thienyl, pyrrolyl and indolyl, each optionally substituted by halogen, lower alkyl or -W-Z as defined under (a); $R_2$ represents hydrogen or lower alkyl; $R_3$ and $R_4$ independently represent hydrogen or lower alkyl; or (d) wherein $R_1$ represents $C_3$-$C_7$-cycloalkyl; $R_2$ represents hydrogen or lower alkyl; $R_3$ and $R_4$ independently represent hydrogen or lower alkyl; or (e) wherein the —$CR_1R_3R_4$ moiety as a single group represents 9-fluorenyl; $R_2$ represents hydrogen or lower alkyl; or (f) wherein $R_1$ represents either phenyl or $C_5$–$C_7$-cyclo-alkyl substituted by a substituent -W-Z in which W represents lower alkylene and Z represents hydroxy; $R_2$ represents hydrogen or lower alkyl; $R_3$ and $R_4$ independently represent hydrogen or lower alkyl; or (g) wherein $R_1$ represents phenyl substituted by -W-Z, in which W represents lower alkylene or lower alkenylene and Z represents phenyl or $C_5$–$C_7$ cycloalkyl; $R_2$ represents hydrogen or lower alkyl; $R_3$ and $R_4$ independently represent hydrogen or lower alkyl; or (h) wherein $R_1$ represents $C_5$–$C_7$-cycloalkyl substituted by a substituent-W-Z in which W represents a direct bond or lower alkylene and Z represents carboxy or carboxy derivatized in the form of a pharmaceutically acceptable ester or amide, or substituted by one or two of lower alkyl, hydroxy, lower alkanoyloxy or lower alkoxy, or substituted by lower alkylenedioxy in which the two oxygen atoms are attached to the same carbon atom or on adjacent carbon atoms; $R_2$ represents hydrogen or lower alkyl; $R_3$ and $R_4$ independently represent hydrogen or lower alkyl; or (i) wherein $R_1$ represents bicycloheptyl optionally substituted by lower alkyl, bicycloheptenyl optionally substituted by lower alkyl, or adamantyl; $R_2$ represents hydrogen or lower alkyl; $R_3$ and $R_4$ independently represent hydrogen or lower alkyl; or (j) wherein $R_1$ represents cyclohexenyl or cyclohexenyl substituted by lower alkyl; $R_2$ represents hydrogen or lower alkyl; $R_3$ and $R_4$ independently represent hydrogen or lower alkyl; or (k) wherein $R_1$ represents tetrahydropyranyl or tetrahydrothiopyranyl; $R_2$ represents a hydrogen or lower alkyl; $R_3$ and $R_4$ independently represent hydrogen or lower alkyl;

or a pharmaceutically acceptable salt thereof.

3. A compound according to claim 2 of formula II wherein $R_2$ and $R_4$ represent hydrogen; $R_3$ represents hydrogen or lower alkyl; and $R_1$ represents:

phenyl substituted by a substituent -W-Z in which W represents a direct bond, lower alkenylene, lower alkylene, thio-lower alkylene or oxy-lower alkylene and Z represents cyano, carboxy or carboxy derivatized in the form of a pharmaceutically acceptable ester or amide, $C_5$–$C_7$-cycloalkyl, $C_5$–$C_7$-cycloalkyl substituted by a substituent -W-Z in which W represents a direct bond or lower alkylene and Z represents carboxy or carboxy derivatized in the form of a pharmaceutically acceptable ester or amide, or $C_5$–$C_7$-cyclalkyl substituted by one or two of lower alkyl, hydroxy, lower alkanoyloxy or lower alkoxy, or substituted by lower alkylenedioxy in which the two oxygen atoms are attached to the same carbon atom or on adjacent carbon atoms, bicycloheptyl optionally substituted by lower alkyl, bicycloheptenyl optionally substituted by lower alkyl, adamantyl, cyclohexenyl optionally substituted by lower alkyl, tetrahydropyranyl or tetrahydrothiopyranyl; or a pharmaceutically acceptable salt thereof.

4. A compound according to claim 3 of formula II wherein $R_1$ represents phenyl monosubstituted by a substituent -W-Z in which W represents a direct bond, straight chain or branched $C_1$–$C_4$-alkylene, thio-$C_1$–$C_3$-alkylene or oxy-$C_1$–$C_3$-alkylene, and Z represents cyano, carboxy, lower alkoxycarbonyl, carbamoyl, N-mono- or N,N-di-lower alkylcarbamoyl; $R_2$ and $R_3$ independently represent hydrogen or $C_1$–$C_4$-alkyl; $R_4$ represents hydrogen; or a pharmaceutically acceptable salt thereof.

5. A compound according to claim 4 wherein W represents straight chain or branched $C_2$–$C_4$-alkylene or oxy-straight chain or branched $C_1$–$C_3$-alkylene in each of which the phenyl ring and Z are separated by a chain of two or three atoms.

6. A compound according to claim 3 of the formula II wherein $R_1$ represents cyclohexyl or cyclopentyl; $R_2$ and $R_4$ represents hydrogen; $R_3$ represents hydrogen or $C_1$–$C_4$-alkyl; or a pharmaceutically acceptable salt thereof.

7. A compound according to claim 3 of the formula II wherein $R_1$ represents 1-cyclohexenyl; $R_2$ and $R_4$ represent hydrogen; $R_3$ represents hydrogen or $C_1$–$C_4$-alkyl; or a pharmaceutically acceptable salt thereof.

8. A compound according to claim 3 of the formula II wherein $R_1$ represents unsubstituted or lower alkyl substituted bicyclo[2.2.1]heptyl; $R_2$, $R_3$ and $R_4$ represent hydrogen; or a pharmaceutically acceptable salt thereof.

9. A compound according to claim 3 of the formula II wherein $R_1$ represents 2-norbornanyl; $R_2$, $R_3$ and $R_4$ represent hydrogen; or a pharmaceutically acceptable salt thereof.

10. A compound according to claim 3 of the formula II wherein $R_1$ represents 1-adamantyl; $R_2$, $R_3$ and $R_4$ represent hydrogen; or a pharmaceutically acceptable salt thereof.

11. A compound according to claim 4 of the formula

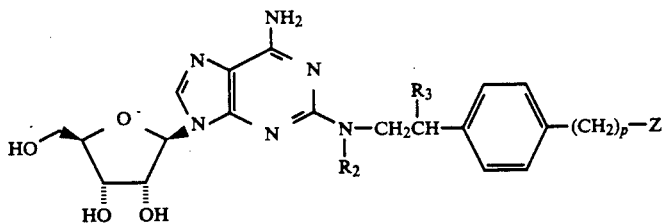

wherein $R_2$ and $R_3$ independently represent hydrogen or $C_1$–$C_4$-alkyl; p represents the integer 1 or 2; Z represents phenyl, carboxy, lower alkoxycarbonyl, carbamoyl, N-mono- or N,N-di-lower alkylcarbamoyl; or a pharmaceutically acceptable salt thereof.

12. A compound according to claim 1 of the formula IIa

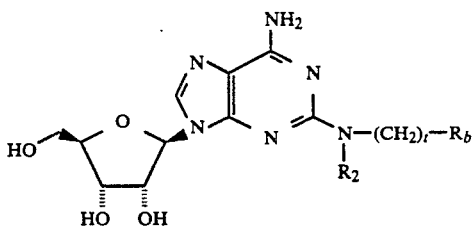

wherein $R_2$ represents hydrogen or lower alkyl; t represents the integer 3, 4, 5 or 6; and $R_b$ represents (a) $C_3$–$C_7$-cycloalkyl optionally substituted by lower alkyl;
(b) cyclohexenyl optionally substituted by lower alkyl;
(c) bicycloheptyl optionally substituted by lower alkyl;
(d) bicycloheptenyl optionally substituted by lower alkyl;
(e) a heterocyclic aromatic radical selected from pyridyl, thienyl, pyrrolyl and indolyl, each optionally substituted by lower alkyl or halogen; or
(f) phenyl substituted by halogen, lower alkyl, lower alkoxy, trifluoromethyl, cyano, carboxy, lower alkoxycarbonyl, carbamoyl, N-mono- or N,N-di-lower alkylcarbamoyl; or a pharmaceutically acceptable salt thereof.

13. A compound according to claim 12 wherein $R_2$ represents hydrogen.

14. A compound according to claim 1 of the formula

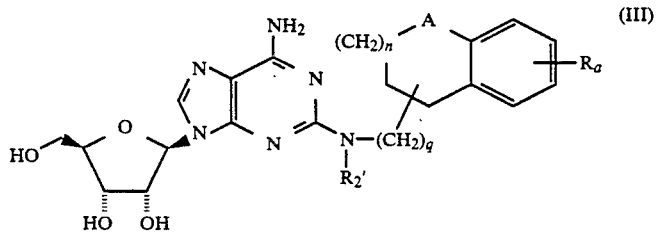

in which A represents methylene, oxy or thio, n represents zero or one, q represents zero, one or two, and $R_a$ represents hydrogen, lower alkyl, lower alkoxy, halogen or -W-Z in which W represents a direct bond, lower alkenylene, lower alkylene, thio-lower alkylene or oxy-lower alkylene, and Z represents cyano, carboxy, carboxy derivatized in the form of a pharmaceutically acceptable ester or carboxy derivatized in the form of a pharmaceutically acceptable amide; and $R_2'$ represents hydrogen or lower alkyl; or a pharmaceutically acceptable salts thereof.

15. A compound according to claim 14 of formula III wherein n represents the integer 1; q is zero; A represents a direct bond, methylene, oxy or thio; $R_a$ represents hydrogen, lower alkyl, lower alkoxy, hydroxy, halogen, or -W-Z in which W represents a direct bond, $C_1$–$C_4$-alkylene, thio-$C_1$–$C_3$-alkylene or oxy-$C_1$–$C_3$-alkylene, and Z represents cyano, carboxy, lower alkoxycarbonyl, carbamoyl, N-mono- or N,N-di-lower alkylcarbamoyl; $R_2'$ represents hydrogen; or a pharmaceutically acceptable salt thereof.

16. A compound according to claim 6 of formula II wherein $R_1$ represents cyclohexyl; $R_2$ and $R_4$ represent hydrogen; $R_3$ represents hydrogen or $C_1$–$C_4$-alkyl; or a pharmaceutically acceptable salt thereof.

17. A compound according to claim 7 being 2-[2-(1-cyclohexenyl)-ethylamino]-adenosine or a pharmaceutically acceptable salt thereof.

18. A compound according to claim 6 being 2-(2-cyclohexylethylamino)-adenosine or a pharmaceutically acceptable salt thereof.

19. A compound according to claim 11 being 2-[p-(2-carboxyethyl)-2-phenylethylamino]-adenosine or a pharmaceutically acceptable salt thereof.

20. A compound according to claim 14 being 2-(2-indanylamino)-adenosine or a pharmaceutically acceptable salt thereof.

21. A pharmaceutical composition suitable for administration to a mammal comprising an effective antihypertensive amount of a compound of claim 1 in combination with one or more pharmaceutically acceptable carriers.

22. A method of treating hypertension in mammals comprising the administration to a mammal in need thereof of an effective antihypertensive amount of a compound of the formula I

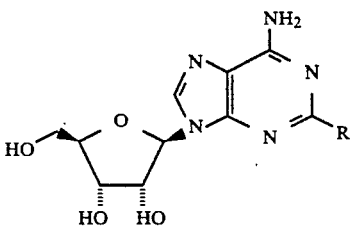

in which the substituent R represents

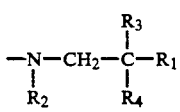

(a) wherein $R_1$ represents phenyl substituted by a substituent -W-Z in which W represents a direct bond, lower alkykene, lower alkylene, thio-lower alkylene or oxy-lower alkylene an Z represents cyano, carboxy or carboxy derivatized in the form of a pharmaceutically acceptable ester or amide; $R_2$ represents hydrogen or lower alkyl; $R_3$ and $R_4$ independently represent hydrogen or lower alkyl; or
(b) wherein $R_1$ represents phenyl or phenyl substituted by one to three of lower alkyl, lower alkoxy, hydroxy, lower alkanoyloxy, halogen, benzyloxy or trifluoromethyl; $R_2$ represents hydrogen or lower alkyl; $R_3$ represent hydrogen, lower alkyl or hydroxy, and $R_4$ represents hydrogen or lower alkyl, with the proviso that $R_2$ does not represent hydrogen if both $R_3$ and $R_4$ represent hydrogen; or (c) wherein $R_1$ represents a heterocyclic aromatic radical selected from pyridyl, thienyl, pyrrolyl and indolyl, each optionally substituted by halogen, lower alkyl or -W-Z as defined under (a); $R_2$ represents hydrogen or lower alkyl; $R_3$ and $R_4$ independently represent hydrogen or lower alkyl; or (d) wherein $R_1$ represents $C_3$–$C_7$-cycloalkyl; $R_2$ represents hydrogen or lower alkyl; $R_3$ and $R_4$ independently represent hydrogen or lower alkyl; or (e) wherein the —$CR_1R_3R_4$ moiety as a single group represents 9-fluorenyl; $R_2$ represents hydrogen or lower alkyl; or (f) wherein $R_1$ represents either phenyl or $C_5$–$C_7$-cycloalkyl substituted by a substituent -W-Z in which W represents lower alkylene and Z represents hydroxy; $R_2$ represents hydrogen or lower alkyl; $R_3$ and $R_4$ independently represent hydrogen or lower alkyl; or (g) wherein $R_1$ represents phenyl substituted by -W-Z, in which W represents lower alkylene or lower alkenylene and Z represents phenyl or $C_5$–$C_7$ cycloalkyl; $R_2$ represents hydrogen or lower alkyl; $R_3$ and $R_4$ independently represent hydrogen or lower alkyl; or (h) wherein $R_1$ represents $C_5$–$C_7$-cycloalkyl substituted by a substituent -W-Z in which W represents a direct bond or lower alkylene and Z represents carboxy or carboxy derivatized in the form of a pharmaceutically acceptable ester or amide, or substituted by one or two of lower alkyl, hydroxy, lower alkanoyloxy or lower alkoxy, or substituted by lower alkylenedioxy in which the two oxygen atoms are attached to the same carbon atom or on adjacent carbon atoms; $R_2$ represents hydrogen or lower alkyl; $R_3$ and $R_4$ independently represent hydrogen or lower alkyl; or (i) wherein $R_1$ represents bicycloheptyl optionally substituted by lower alkyl, bicycloheptenyl optionally substituted by lower alkyl, or adamantyl; $R_2$ represents hydrogen or lower alkyl; $R_3$ and $R_4$ independently represent hydrogen or lower alkyl; or (j) wherein $R_1$ represents cyclohexenyl or cyclohexenyl substituted by lower alkyl; $R_2$ represents hydrogen or lower alkyl; $R_3$ and $R_4$ independently represent hydrogen or lower alkyl; or (k) wherein $R_1$ represents tetrahydropyranyl or terahydrothiopyranyl; $R_2$ represents hydrogen or lower alkyl; $R_3$ and $R_4$ independently represent hydrogen or lower alkyl;

or a compound of formula I in which the substituent R represents

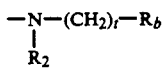

wherein $R_2$ represents hydrogen or lower alkyl; t represents the integer 3, 4, 5 or 6; and $R_b$ represents (a) $C_3$–$C_7$-cycloalkyl optionally substituted by lower alkyl;

(b) cyclohexenyl optionally substituted by lower alkyl;

(c) bicycloheptyl optionally substituted by lower alkyl;

(d) bicycloheptenyl optionally substituted by lower alkyl;

(e) a heterocyclic aromatic radical selected from pyridyl, thienyl, pyrrolyl and indolyl, each optionally substituted by lower alkyl or halogen; or (f) phenyl or phenyl substituted by halogen, lower alkyl, lower alkoxy, trifluoromethyl, cyano, carboxy, lower alkoxycarbonyl, carbamoyl, N-mono- or N,N-di-lower alkylcarbamoyl; or a compound of formula I in which the substituent R represents

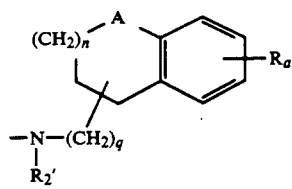

in which A represents methylene, oxy or thio, n represents zero or one, q represents zero, one or two, and $R_a$ represents hydrogen, lower alkyl, lower alkoxy, halogen or -W-Z in which W represents a direct bond, lower alkenylene, lower alkylene, thio-lower alkylene or oxy-lower alkylene, and Z represents cyano, carboxy, carboxy derivatized in the form of a pharmaceutically acceptable ester or carboxy derivatized in the form of a pharmaceutically acceptable amide; and $R_2'$ represents hydrogen or lower alkyl; or a pharmaceutically acceptable salt thereof; and wherein in the above definitions carboxy derivatized in the form of a pharmaceutically acceptable ester represents lower alkoxycarbonyl; carboxy derivatized in form of a pharmaceutically acceptable amide represents carbamoyl, mono-N-lower alkylcarbamoyl or N,N-di-lower alkylcarbamoyl; or of a pharmaceutical composition comprising a said compound.

* * * * *

UNITED STATES PATENT AND TRADEMARK OFFICE
CERTIFICATE OF CORRECTION

PATENT NO. : 5,034,381
DATED : Jul.23, 1991
INVENTOR(S) : Hutchison et al.

It is certified that error appears in the above-identified patent and that said Letters Patent is hereby corrected as shown below:

Column 26:

Claim 1, formula I should read:

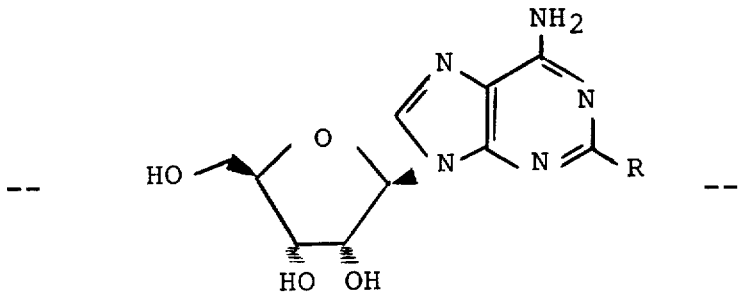

Column 32:

Claim 22, formula I should read:

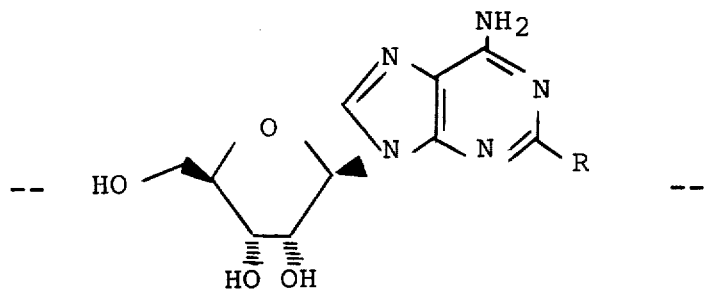

Claim 22, line 56 should read:

-- bond, lower alkenylene, lower alkylene, thio-lower --

UNITED STATES PATENT AND TRADEMARK OFFICE
CERTIFICATE OF CORRECTION

PATENT NO. : 5,034,381

DATED : July 23, 1991

INVENTOR(S) : Alan J. Hutchison, et al.

It is certified that error appears in the above-identified patent and that said Letters Patent is hereby corrected as shown below:

Column 32:

Claim 22, line 56 should read:

-- bond, lower alkenylene, lower alkylene, thio-lower --

Signed and Sealed this

Ninth Day of February, 1993

Attest:

STEPHEN G. KUNIN

Attesting Officer

Acting Commissioner of Patents and Trademarks